(12) United States Patent
Kusens

(10) Patent No.: US 10,482,321 B2
(45) Date of Patent: Nov. 19, 2019

(54) METHODS AND SYSTEMS FOR IDENTIFYING THE CROSSING OF A VIRTUAL BARRIER

(71) Applicant: CERNER INNOVATION, INC., Kansas City, KS (US)

(72) Inventor: Michael Kusens, Cooper City, FL (US)

(73) Assignee: Cerner Innovation, Inc., Kansas City, KS (US)

( * ) Notice: Subject to any disclaimer, the term of this patent is extended or adjusted under 35 U.S.C. 154(b) by 64 days.

(21) Appl. No.: 15/857,696

(22) Filed: Dec. 29, 2017

(65) Prior Publication Data

US 2019/0205630 A1    Jul. 4, 2019

(51) Int. Cl.
G06K 9/00    (2006.01)
G06T 7/73    (2017.01)
A61B 5/11    (2006.01)

(52) U.S. Cl.
CPC ........ *G06K 9/00369* (2013.01); *A61B 5/1113* (2013.01); *A61B 5/1115* (2013.01); *G06K 9/00771* (2013.01); *G06T 7/73* (2017.01); *G06T 2207/30196* (2013.01); *G06T 2210/12* (2013.01)

(58) Field of Classification Search
None
See application file for complete search history.

(56) References Cited

U.S. PATENT DOCUMENTS

| | | |
|---|---|---|
| 1,860,487 A | 5/1932 | Thauss et al. |
| 4,669,263 A | 6/1987 | Sugiyama |
| 4,857,716 A | 8/1989 | Gombrich et al. |
| 5,031,228 A | 7/1991 | Lu |
| 5,276,432 A | 1/1994 | Travis |
| 5,448,221 A | 9/1995 | Weller |
| 5,482,050 A | 1/1996 | Smokoff et al. |
| 5,592,153 A | 1/1997 | Welling et al. |
| 5,798,798 A | 8/1998 | Rector et al. |
| 5,838,223 A | 11/1998 | Gallant et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,160,478 A | 12/2000 | Jacobsen et al. |
| 6,174,283 B1 | 1/2001 | Nevo et al. |

(Continued)

FOREIGN PATENT DOCUMENTS

| | | |
|---|---|---|
| DE | 19844918 A1 | 4/2000 |
| WO | 2007/081629 A2 | 7/2007 |

(Continued)

OTHER PUBLICATIONS

US 9,948,899 B1, 04/2018, Kusens (withdrawn)

(Continued)

*Primary Examiner* — Soo Jin Park
(74) *Attorney, Agent, or Firm* — Shook, Hardy & Bacon, LLP

(57) ABSTRACT

Systems, methods and media are disclosed for identifying the crossing of a virtual barrier. A person in a 3D image of a room may be circumscribed by a bounding box. The position of the bounding box may be monitored over time, relative to the virtual barrier. If the bounding box touches or crosses the virtual barrier, an alert may be sent to the person being monitored, a caregiver or a clinician.

19 Claims, 10 Drawing Sheets

(56) References Cited

U.S. PATENT DOCUMENTS

| | | |
|---|---|---|
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,614,349 B1 | 9/2003 | Proctor et al. |
| 6,727,818 B1 | 4/2004 | Wildman et al. |
| 6,804,656 B1 | 10/2004 | Rosenfeld et al. |
| 7,015,816 B2 | 3/2006 | Wildman et al. |
| 7,122,005 B2 | 10/2006 | Shusterman |
| 7,154,397 B2 | 12/2006 | Zerhusen et al. |
| 7,237,287 B2 | 7/2007 | Weismiller et al. |
| 7,323,991 B1 | 1/2008 | Eckert et al. |
| 7,408,470 B2 | 8/2008 | Wildman et al. |
| 7,420,472 B2 | 9/2008 | Tran |
| 7,430,608 B2 | 9/2008 | Noonan et al. |
| 7,502,498 B2 | 3/2009 | Wen et al. |
| 7,612,679 B1 | 11/2009 | Fackler et al. |
| 7,669,263 B2 | 3/2010 | Menkedick et al. |
| 7,715,387 B2 | 5/2010 | Schuman |
| 7,724,147 B2 | 5/2010 | Brown |
| 7,756,723 B2 | 7/2010 | Rosow et al. |
| 7,890,349 B2 | 2/2011 | Cole et al. |
| 7,893,842 B2 | 2/2011 | Deutsch |
| 7,895,055 B2 | 2/2011 | Schneider et al. |
| 7,908,153 B2 | 3/2011 | Scherpbier et al. |
| 7,945,457 B2 | 5/2011 | Zaleski |
| 7,962,544 B2 | 6/2011 | Torok et al. |
| 7,972,140 B2 | 7/2011 | Renaud |
| 8,108,036 B2 | 1/2012 | Tran |
| 8,123,685 B2 | 2/2012 | Brauers et al. |
| 8,128,596 B2 | 3/2012 | Carter |
| 8,224,108 B2 | 7/2012 | Steinberg et al. |
| 8,237,558 B2 | 8/2012 | Seyed Momen et al. |
| 8,273,018 B1 | 9/2012 | Fackler et al. |
| 8,432,263 B2 | 4/2013 | Kunz |
| 8,451,314 B1 | 5/2013 | Cline et al. |
| 8,529,448 B2 | 9/2013 | McNair |
| 8,565,500 B2 | 10/2013 | Neff |
| 8,620,682 B2 | 12/2013 | Bechtel et al. |
| 8,655,680 B2 | 2/2014 | Bechtel et al. |
| 8,700,423 B2 | 4/2014 | Eaton, Jr. et al. |
| 8,727,981 B2 | 5/2014 | Bechtel et al. |
| 8,769,153 B2 | 7/2014 | Dziubinski |
| 8,890,937 B2 | 11/2014 | Skubic et al. |
| 8,902,068 B2 | 12/2014 | Bechtel et al. |
| 8,917,186 B1 | 12/2014 | Grant |
| 8,953,886 B2 | 2/2015 | King et al. |
| 9,072,929 B1 | 7/2015 | Rush et al. |
| 9,129,506 B1 | 9/2015 | Kusens |
| 9,147,334 B2 | 9/2015 | Long et al. |
| 9,159,215 B1* | 10/2015 | Kusens .................. G08B 21/22 |
| 9,269,012 B2 | 2/2016 | Fotland |
| 9,292,089 B1 | 3/2016 | Sadek |
| 9,305,191 B2 | 4/2016 | Long et al. |
| 9,408,561 B2 | 8/2016 | Stone et al. |
| 9,489,820 B1* | 11/2016 | Kusens .................. A61B 5/746 |
| 9,519,969 B1* | 12/2016 | Kusens ................ G08B 21/043 |
| 9,524,443 B1* | 12/2016 | Kusens .................. G06F 16/51 |
| 9,536,310 B1 | 1/2017 | Kusens |
| 9,538,158 B1 | 1/2017 | Rush et al. |
| 9,563,955 B1 | 2/2017 | Kamarshi et al. |
| 9,597,016 B2 | 3/2017 | Stone et al. |
| 9,729,833 B1 | 8/2017 | Kusens |
| 9,741,227 B1 | 8/2017 | Kusens |
| 9,892,310 B2 | 2/2018 | Kusens et al. |
| 9,892,311 B2 | 2/2018 | Kusens et al. |
| 9,892,611 B1* | 2/2018 | Kusens ................ G08B 21/043 |
| 9,905,113 B2 | 2/2018 | Kusens |
| 10,055,961 B1* | 8/2018 | Johnson ............... G08B 29/186 |
| 10,078,956 B1 | 9/2018 | Kusens |
| 10,090,068 B2 | 10/2018 | Kusens |
| 10,091,463 B1 | 10/2018 | Kusens |
| 10,096,223 B1 | 10/2018 | Kusens |
| 10,210,378 B2 | 2/2019 | Kusens et al. |
| 10,225,522 B1 | 3/2019 | Kusens |
| 10,276,019 B2* | 4/2019 | Johnson ............... G08B 29/186 |
| 2002/0015034 A1 | 2/2002 | Malmborg |
| 2002/0038073 A1 | 3/2002 | August |
| 2002/0077863 A1 | 6/2002 | Rutledge et al. |
| 2002/0101349 A1 | 8/2002 | Rojas, Jr. |
| 2002/0115905 A1 | 8/2002 | August |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0135390 A1 | 7/2003 | O'Brien et al. |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0052418 A1 | 3/2004 | DeLean |
| 2004/0054760 A1 | 3/2004 | Ewing et al. |
| 2004/0097227 A1 | 5/2004 | Siegel |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0182305 A1 | 8/2005 | Hendrich |
| 2005/0231341 A1 | 10/2005 | Shimizu |
| 2005/0249139 A1 | 11/2005 | Nesbit |
| 2006/0004606 A1 | 1/2006 | Wendl et al. |
| 2006/0047538 A1 | 3/2006 | Condurso et al. |
| 2006/0049936 A1 | 3/2006 | Collins et al. |
| 2006/0058587 A1 | 3/2006 | Heimbrock et al. |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0145874 A1 | 7/2006 | Fredriksson et al. |
| 2006/0261974 A1 | 11/2006 | Albert et al. |
| 2007/0085690 A1 | 4/2007 | Tran |
| 2007/0118054 A1 | 5/2007 | Pinhas et al. |
| 2007/0120689 A1 | 5/2007 | Zerhusen et al. |
| 2007/0129983 A1 | 6/2007 | Scherpbier et al. |
| 2007/0136102 A1 | 6/2007 | Rodgers |
| 2007/0136218 A1 | 6/2007 | Bauer et al. |
| 2007/0159332 A1 | 7/2007 | Koblasz |
| 2007/0279219 A1 | 12/2007 | Warriner |
| 2007/0296600 A1 | 12/2007 | Dixon et al. |
| 2008/0001735 A1 | 1/2008 | Tran |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0021731 A1 | 1/2008 | Rodgers |
| 2008/0071210 A1 | 3/2008 | Moubayed et al. |
| 2008/0087719 A1 | 4/2008 | Sahud |
| 2008/0106374 A1 | 5/2008 | Sharbaugh |
| 2008/0126132 A1 | 5/2008 | Warner et al. |
| 2008/0228045 A1 | 9/2008 | Gao et al. |
| 2008/0249376 A1 | 10/2008 | Zaleski |
| 2008/0267447 A1 | 10/2008 | Kelusky et al. |
| 2008/0277486 A1 | 11/2008 | Seem et al. |
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1 | 4/2009 | Salgo et al. |
| 2009/0112630 A1 | 4/2009 | Collins, Jr. et al. |
| 2009/0119843 A1 | 5/2009 | Rodgers et al. |
| 2009/0177327 A1 | 7/2009 | Turner et al. |
| 2009/0224924 A1 | 9/2009 | Thorp |
| 2009/0278934 A1 | 11/2009 | Ecker et al. |
| 2009/0322513 A1 | 12/2009 | Hwang et al. |
| 2010/0117836 A1 | 5/2010 | Seyed Momen et al. |
| 2010/0169114 A1 | 7/2010 | Henderson et al. |
| 2010/0169120 A1 | 7/2010 | Herbst et al. |
| 2010/0172567 A1 | 7/2010 | Prokoski |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |

(56) References Cited

U.S. PATENT DOCUMENTS

| | | |
|---|---|---|
| 2011/0018709 A1 | 1/2011 | Kombluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |
| 2011/0035466 A1 | 2/2011 | Panigrahi |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1 | 4/2011 | Aarts |
| 2011/0087125 A1 | 4/2011 | Causevic |
| 2011/0102133 A1 | 5/2011 | Shaffer |
| 2011/0102181 A1 | 5/2011 | Metz et al. |
| 2011/0106560 A1 | 5/2011 | Eaton, Jr. et al. |
| 2011/0106561 A1 | 5/2011 | Eaton, Jr. et al. |
| 2011/0175809 A1 | 7/2011 | Markovic et al. |
| 2011/0190593 A1 | 8/2011 | McNair |
| 2011/0227740 A1 | 9/2011 | Wohltjen |
| 2011/0245707 A1 | 10/2011 | Castle et al. |
| 2011/0254682 A1 | 10/2011 | Sigrist Christensen |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0016295 A1 | 1/2012 | Tsoukalis |
| 2012/0025991 A1 | 2/2012 | O'Keefe et al. |
| 2012/0026308 A1 | 2/2012 | Johnson et al. |
| 2012/0075464 A1 | 3/2012 | Derenne et al. |
| 2012/0092162 A1 | 4/2012 | Rosenberg |
| 2012/0098918 A1 | 4/2012 | Murphy |
| 2012/0140068 A1 | 6/2012 | Monroe et al. |
| 2012/0154582 A1 | 6/2012 | Johnson et al. |
| 2012/0212582 A1 | 8/2012 | Deutsch |
| 2012/0259650 A1 | 10/2012 | Mallon et al. |
| 2012/0314901 A1 | 12/2012 | Hanson et al. |
| 2012/0323090 A1 | 12/2012 | Bechtel et al. |
| 2012/0323591 A1 | 12/2012 | Bechtel et al. |
| 2012/0323592 A1 | 12/2012 | Bechtel et al. |
| 2013/0027199 A1 | 1/2013 | Bonner |
| 2013/0028570 A1 | 1/2013 | Suematsu et al. |
| 2013/0120120 A1 | 5/2013 | Long et al. |
| 2013/0122807 A1 | 5/2013 | Tenarvitz et al. |
| 2013/0127620 A1 | 5/2013 | Siebers et al. |
| 2013/0184592 A1 | 7/2013 | Venetianer et al. |
| 2013/0265482 A1 | 10/2013 | Funamoto |
| 2013/0309128 A1 | 11/2013 | Voegeli et al. |
| 2013/0332184 A1 | 12/2013 | Bumham et al. |
| 2014/0039351 A1 | 2/2014 | Mix et al. |
| 2014/0070950 A1 | 3/2014 | Snodgrass |
| 2014/0081654 A1 | 3/2014 | Bechtel et al. |
| 2014/0085501 A1 | 3/2014 | Tran |
| 2014/0086450 A1 | 3/2014 | Huang et al. |
| 2014/0108041 A1 | 4/2014 | Bechtel et al. |
| 2014/0155755 A1 | 6/2014 | Pinter et al. |
| 2014/0191861 A1 | 7/2014 | Scherrer |
| 2014/0213845 A1 | 7/2014 | Bechtel et al. |
| 2014/0267625 A1 | 9/2014 | Clark et al. |
| 2014/0267736 A1* | 9/2014 | DeLean ............ G08B 13/19613 348/152 |
| 2014/0327545 A1 | 11/2014 | Bolling et al. |
| 2014/0328512 A1* | 11/2014 | Gurwicz .............. G06K 9/6263 382/103 |
| 2014/0333744 A1 | 11/2014 | Baym et al. |
| 2014/0333776 A1* | 11/2014 | Dedeoglu .............. H04N 7/181 348/159 |
| 2014/0354436 A1 | 12/2014 | Nix et al. |
| 2014/0365242 A1 | 12/2014 | Neff |
| 2015/0057635 A1 | 2/2015 | Bechtel et al. |
| 2015/0109442 A1 | 4/2015 | Derenne et al. |
| 2015/0206415 A1 | 7/2015 | Wegelin et al. |
| 2015/0269318 A1 | 9/2015 | Neff |
| 2015/0278456 A1 | 10/2015 | Bermudez Rodriguez et al. |
| 2015/0294143 A1* | 10/2015 | Wells ................ G06K 9/00369 348/159 |
| 2016/0022218 A1 | 1/2016 | Hayes et al. |
| 2016/0070869 A1 | 3/2016 | Portnoy |
| 2016/0093195 A1 | 3/2016 | Ophardt |
| 2016/0127641 A1 | 5/2016 | Gove |
| 2016/0180668 A1 | 6/2016 | Kusens et al. |
| 2016/0183864 A1 | 6/2016 | Kusens et al. |
| 2016/0217347 A1 | 7/2016 | Mineo |
| 2016/0253802 A1 | 9/2016 | Venetianer et al. |
| 2016/0267327 A1 | 9/2016 | Franz et al. |
| 2016/0314258 A1 | 10/2016 | Kusens |
| 2016/0324460 A1 | 11/2016 | Kusens |
| 2016/0360970 A1 | 12/2016 | Tzvieli et al. |
| 2017/0055917 A1 | 3/2017 | Stone et al. |
| 2017/0084158 A1 | 3/2017 | Kusens |
| 2017/0091562 A1 | 3/2017 | Kusens |
| 2017/0109991 A1 | 4/2017 | Kusens |
| 2017/0143240 A1 | 5/2017 | Stone et al. |
| 2017/0193177 A1 | 7/2017 | Kusens |
| 2017/0193279 A1 | 7/2017 | Kusens et al. |
| 2017/0193772 A1 | 7/2017 | Kusens et al. |
| 2017/0195637 A1 | 7/2017 | Kusens et al. |
| 2017/0289503 A1 | 10/2017 | Kusens |
| 2017/0337682 A1 | 11/2017 | Liao et al. |
| 2018/0018864 A1 | 1/2018 | Baker |
| 2018/0068545 A1 | 3/2018 | Kusens |
| 2018/0104409 A1 | 4/2018 | Bechtel et al. |
| 2018/0114053 A1 | 4/2018 | Kusens et al. |
| 2018/0137340 A1 | 5/2018 | Kusens et al. |
| 2018/0144605 A1 | 5/2018 | Kusens |
| 2018/0189946 A1 | 7/2018 | Kusens et al. |
| 2018/0190098 A1 | 7/2018 | Kusens |
| 2018/0357875 A1 | 12/2018 | Kusens |
| 2019/0006046 A1 | 1/2019 | Kusens et al. |
| 2019/0029528 A1 | 1/2019 | Tzvieli et al. |
| 2019/0043192 A1 | 2/2019 | Kusens et al. |
| 2019/0057592 A1 | 2/2019 | Kusens |
| 2019/0122028 A1 | 4/2019 | Kusens et al. |
| 2019/0206218 A1 | 7/2019 | Kusens et al. |

FOREIGN PATENT DOCUMENTS

| | | |
|---|---|---|
| WO | 2009018422 A1 | 2/2009 |
| WO | 2012122002 A1 | 9/2012 |

OTHER PUBLICATIONS

Conaire et al., "Fusion of infrared and visible spectrum video for indoor surveillance", in WIAMIS, Apr. 2005 (Year: 2005).*

Final Office Action received for U.S. Appl. No. 15/395,243, dated Jun. 11, 2019, 18 pages.

Non-Final Office Action received for U.S. Appl. No. 15/134,189, dated May 9, 2019, 30 pages.

Non-Final Office Action dated Jan. 11, 2017 in U.S. Appl. No. 14/611,363, 19 pages.

Non-Final Office Action dated Feb. 23, 2017 in U.S. Appl. No. 14/757,877, 24 pages.

First Action Interview Preinterview Communication dated Feb. 24, 2017 in U.S. Appl. No. 15/395,716, 6 pages.

Notice of Allowance dated Mar. 20, 2017 in U.S. Appl. No. 14/613,866, 11 pages.

Non-Final Office Action dated Apr. 5, 2017 in U.S. Appl. No. 14/623,349, 15 pages.

Non-Final Office Action dated Apr. 11, 2017 in U.S. Appl. No. 15/285,416, 13 pages.

Non-Final Office Action dated Apr. 21, 2017 in U.S. Appl. No. 14/757,593, 9 pages.

Notice of Allowance dated Apr. 21, 2017 in U.S. Appl. No. 14/724,969, 9 pages.

Notice of Allowance dated Apr. 25, 2017 in U.S. Appl. No. 14/727,434, 9 pages.

Non-Final Office Action dated Apr. 27, 2017 in U.S. Appl. No. 15/395,526, 16 pages.

Final Office Action dated Apr. 28, 2017 in U.S. Appl. No. 14/611,363, 20 pages.

Non-Final Office Action dated May 8, 2017 in U.S. Appl. No. 15/395,250, 19 pages.

(56) References Cited

OTHER PUBLICATIONS

Non-Final Office Action dated May 31, 2017 in U.S. Appl. No. 14/599,498, 24 pages.
Notice of Allowance dated Jul. 5, 2017 in U.S. Appl. No. 14/727,434, 9 pages.
Notice of Allowance dated Jul. 24, 2017 in U.S. Appl. No. 15/395,716, 5 pages.
Non-Final Office Action dated Aug. 16, 2017 in U.S. Appl. No. 14/757,593, 8 pages.
Final Office Action dated Aug. 23, 2017 in U.S. Appl. No. 15/285,416, 16 pages.
Notice of Allowance dated Sep. 21, 2017 in U.S. Appl. No. 15/395,526, 13 pages.
Notice of Allowance dated Sep. 26, 2017 in U.S. Appl. No. 15/395,250, 13 pages.
Final Office Action dated Sep. 29, 2017 in U.S. Appl. No. 14/757,877, 22 pages.
Final Office Action dated Oct. 4, 2017 in U.S. Appl. No. 14/623,349, 30 pages.
Notice of Allowance dated Oct. 10, 2017 in U.S. Appl. No. 14/727,434, 9 pages.
Final Office Action dated Oct. 12, 2017 in U.S. Appl. No. 14/599,498, 28 pages.
Notice of Allowance dated Oct. 20, 2017 in U.S. Appl. No. 15/279,054, 14 pages.
First Action Interview Pre-Interview Communication dated Nov. 22, 2017 in U.S. Appl. No. 15/134,189, 4 pages.
Virtual Patient Observation: Centralize Monitoring of High-Risk Patients with Video—Cisco Video Surveillance Manager, htttps://www.cisco.com/c/en/us/products/collateral/physical-security/video-surveillance-manager/white paper_C11-715263.pdf.
Notice of Allowance dated Dec. 6, 2017 in U.S. Appl. No. 15/395,716, 5 pages.
Final Office Action dated Dec. 12, 2017 in U.S. Appl. No. 14/575,850, 10 pages.
Notice of Allowance dated Dec. 29, 2017 in U.S. Appl. No. 14/611,363, 11 pages.
Notice of Allowance dated Feb. 12, 2018 in U.S. Appl. No. 14/623,349, 11 pages.
Final Office Action dated Feb. 16, 2018 in U.S. Appl. No. 14/757,593, 8 pages.
First Action Interview Office Action dated Feb. 22, 2018 in U.S. Appl. No. 15/134,189, 4 pages.
Non-Final Office Action dated Feb. 22, 2018 in U.S. Appl. No. 14/599,498, 24 pages.
Non-Final Office Action dated Mar. 14, 2018 in U.S. Appl. No. 14/757,877, 13 pages.
Non Final Office Action received for U.S. Appl. No. 16/107,567, dated Mar. 29, 2019, 8 pages.
Non-Final Office Action received for U.S. Appl. No. 15/395,762, dated May 1, 2019, 27 pages.
Non-Final Office Action received for U.S. Appl. No. 15/856,419, dated May 2, 2019, 8 pages.
Notice of Allowance dated Jun. 18, 2018 in U.S. Appl. No. 14/623,349, 11 pages.
Notice of Allowance dated Jul. 18, 2018 in U.S. Appl. No. 14/599,498, 6 pages.
Non-Final Office Action dated Aug. 15, 2018 in U.S. Appl. No. 15/910,632, 7 pages.
Non-Final Office Action dated Sep. 10, 2018 in U.S. Appl. No. 15/910,645, 11 pages.
Pending U.S. Application by same inventor Neil Kusens, U.S. Appl. No. 14/599,498, filed Jan. 17, 2015, entitled "Method and System for Determining Whether an Individual Takes Appropriate Measures to Prevent the Spread of Healthcare Associated Infections".
Pending U.S. Application by same inventor Neil Kusens, U.S. Appl. No. 14/611,363, filed Feb. 2, 2015, entitled "Method and System for Determining Whether an Individual Takes Appropriate Measures to Prevent the Spread of Healthcare Associated Infections".
Pending U.S. Application by same inventor Neil Kusens, U.S. Appl. No. 14/623,349, filed Feb. 16, 2015, entitled "Method for Determining Whether an Individual Enters a Prescribed Virtual Zone Using 3D Blob Detection".
Tom Mooney, "Rhode Island ER first to test Google Glass on medical conditions", http://www.ems1.com/ems-products/cameras-video/articles/1860487-Rhode-Island-ER-first . . . printed on Mar. 11, 2014.
Non-Final Office Action dated Dec. 30, 2013 in U.S. Appl. No. 13/543,816, 9 pages.
Final Office Action dated Jun. 17, 2014 in U.S. Appl. No. 13/543,816, 15 pages.
Non-Final Office Action dated Jul. 16, 2014 in U.S. Appl. No. 14/084,588, 12 pages.
Non-Final Office Action dated Dec. 1, 2014 in U.S. Appl. No. 13/543,816, 18 pages.
Final Office Action dated Dec. 19, 2014 in U.S. Appl. No. 14/084,588, 24 pages.
Notice of Allowance dated Jun. 5, 2015 in U.S. Appl. No. 13/543,816, 5 pages.
Non-Final Office Action dated Oct. 7, 2015 in U.S. Appl. No. 14/339,397, 16 pages.
Non-Final Office Action dated Feb. 11, 2016 in U.S. Appl. No. 14/724,969, 14 pages.
Non-Final Office Action dated Mar. 11, 2016 in U.S. Appl. No. 14/575,850, 10 pages.
Non-Final Office Action dated May 23, 2016 in U.S. Appl. No. 14/743,499, 5 pages.
Notice of Allowance dated May 31, 2016 in U.S. Appl. No. 14/743,447, 8 pages.
Notice of Allowance dated Jun. 22, 2016 in U.S. Appl. No. 14/728,762, 4 pages.
Notice of Allowance dated Jul. 18, 2016 in U.S. Appl. No. 14/743,264, 16 pages.
Final Office Action dated Jul. 28, 2016 in U.S. Appl. No. 14/724,969, 26 pages.
Notice of Allowance dated Sep. 19, 2016 in U.S. Appl. No. 14/743,499, 5 pages.
Non-Final Office Action dated Sep. 23, 2016 in U.S. Appl. No. 14/727,434, 9 pages.
Notice of Allowance dated Nov. 9, 2016 in U.S. Appl. No. 14/743,264, 14 pages.
Raheja, et al., "Human Facial Expression Detection From Detected in CapturedImage Using Back Propagation Neural Network", International Journal of Computer Science and Information Technology (IJCSIT), vol. 2, No. 1, Feb. 2010, 8 pages.
Pending U.S. Application by same inventor Neil Kusens, U.S. Appl. No. 14/575,850, filed Dec. 18, 2014, entitled "Method and Process for Determining Whether an Individual Suffers a Fall Requiring Assistance".
Notice of Allowance dated Jun. 27, 2016 in U.S. Appl. No. 14/728,762, 13 pages.
Notice of Allowance dated Aug. 26, 2016 in U.S. Appl. No. 14/743,447, 5 pages.
Notice of Allowance dated Oct. 14, 2016 in U.S. Appl. No. 14/743,264, 14 pages.
Notice of Allowance dated Nov. 14, 2016 in U.S. Appl. No. 14/743,447, 5 pages.
Notice of Allowance dated Dec. 23, 2016 in U.S. Appl. No. 14/724,969, 5 pages.
Non-Final Office Action dated Apr. 14, 2017 in U.S. Appl. No. 15/396,263, 18 pages.
Notice of Allowance dated Apr. 19, 2017 in U.S. Appl. No. 15/395,716, 5 pages.
Notice of Allowance dated Apr. 21, 2017 in U.S. Appl. No. 14/724,969, 8 pages.
Final Office Action dated Oct. 18, 2017 in U.S. Appl. No. 15/396,263, 20 pages.
Notice of Allowance dated Nov. 27, 2017 in U.S. Appl. No. 15/279,054, 2 pages.
Notice of Allowance dated Jan. 18, 2018 in U.S. Appl. No. 15/279,054, 2 pages.

(56) References Cited

OTHER PUBLICATIONS

Non-Final Office Action dated Feb. 7, 2018 in U.S. Appl. No. 15/396,263, 19 pages.
Non-Final Office Action dated Mar. 12, 2018 in U.S. Appl. No. 15/285,416, 20 pages.
Non-Final Office Action dated May 2, 2018 in U.S. Appl. No. 15/728,110, 8 pages.
Non-Final Office Action dated May 7, 2018 in U.S. Appl. No. 14/611,363, 6 pages.
Non-Final Office Action dated May 8, 2018 in U.S. Appl. No. 15/148,151, 5 pages.
Notice of Allowance dated May 9, 2018 in U.S. Appl. No. 15/395,716, 5 pages.
First Action Interview Pre-Interview Communication dated May 21, 2018 in U.S. Appl. No. 15/910,645, 14 pages.
Non-Final Office Action dated May 31, 2018 in U.S. Appl. No. 15/395,762, 24 pages.
Non-Final Office Action dated May 31, 2018 in U.S. Appl. No. 15/848,621, 23 pages.
Notice of Allowance dated Jun. 4, 2018 in U.S. Appl. No. 14/157,593, 5 pages.
Non-Final Office Action dated Jun. 8, 2018 in U.S. Appl. No. 15/628,318, 9 new pages.
Notice of Allowance dated Jun. 13, 2018 in U.S. Appl. No. 14/575,850, 5 pages.
Notice of Allowance dated Jun. 19, 2018 in U.S. Appl. No. 15/395,716, 2 pages.
Final Office Action dated Jul. 5, 2018 in U.S. Appl. No. 15/285,416, 8 pages.
Final Office Action dated Jul. 12, 2018 in U.S. Appl. No. 15/134,189, 23 pages.
Notice of Allowance dated Jul. 13, 2018 in U.S. Appl. No. 15/396,263, 9 pages.
Notice of Allowance dated Jul. 23, 2018 in U.S. Appl. No. 15/728,110, 15 pages.
Non Final Office Action received for U.S. Appl. No. 15/395,243, dated Feb. 14, 2019, 14 pages.
Non Final Office Action received for U.S. Appl. No. 16/216,210, dated Feb. 13, 2019, 29 pages.
Notice of Allowance received for U.S. Appl. No. 16/380,013, dated Jul. 10, 2019, 10 pages.

\* cited by examiner

METHODS AND SYSTEMS FOR IDENTIFYING THE CROSSING OF A VIRTUAL BARRIER

TECHNICAL FIELD

This disclosure relates generally to computerized methods and systems for identifying the crossing of a virtual barrier.

BACKGROUND

Patients in institutional, home-like or in-home care are often monitored for a variety of behaviors. One concern is the possibility of a patient falling, for example, while trying to get out of bed without assistance. Falls can cause significant harm to the patient, interfere with medical care for other issues, and increase burdens on caregivers or medical providers for the patient. Another concern is a patient touching, removing or otherwise disturbing medical equipment. Self-adjustment or removal of nasogastral tubes or intravenous lines, for example, can cause harm to the patient, impede medical treatment, and add to the heavy burdens of a caregiver or medical practitioner who must restore the medical equipment. For children or patients with dementia, it may be desirable to know if a patient is leaving a room or other space without a chaperone who can insure the patient's safety. It would be desirable to assist caregivers and medical providers with the monitoring for these kinds of events, to help improve patient safety and reduce the burden on caregivers and medical providers.

BRIEF SUMMARY

This brief summary is meant to present an overview of concepts related to this disclosure, and is expressly not meant to define or identify key elements of the disclosure in isolation from the remainder of the disclosure, including the figures.

This disclosure generally relates to systems, methods, and media for identifying the crossing of a virtual barrier. The systems and methods may be computerized and, once configured, may operate without human engagement or intervention unless or until an alarm condition arises.

In some aspects, this disclosure relates to a method of identifying the crossing of a virtual barrier. The method comprises receiving image data for a room from one or more 3D motion sensors. The method comprises configuring a virtual barrier within the room, by a computerized monitoring system. The method comprises classifying an object within the room as a person. The method comprises creating a bounding box to circumscribe at least a portion of the person. The method comprises monitoring a position of the bounding box over time and relative to the virtual barrier. The virtual barrier may be configured automatically by the computerized monitoring system. The virtual barrier may be configured by the computerized monitoring system based on input from a human user. The method may further comprise sending an alert to a computerized communication system if the bounding box touches or crosses the virtual barrier. Upon receiving the alert, the computerized communication system notifies the person, a caregiver, or clinician that the virtual barrier has been crossed. An alert may be sent to the computerized communication system only if a specified minimum portion of the bounding box crosses the virtual barrier. The image data may be sent to a centralized monitoring station. The centralized monitoring station may display human-intelligible images from the image data.

In some aspects, this disclosure relates to a system for identifying the crossing of a virtual barrier. The system comprises a computerized monitoring system in communication with one or more 3D motion sensors and a computerized communication system. The computerized monitoring system is configured to receive image data from the one or more 3D motion sensors, configure a virtual barrier, analyze the image data to create a bounding box around a person in the image data, and send an alert to the computerized communication system if the bounding box touches or crosses the virtual barrier. The system may further comprise a user input device. The computerized monitoring system may be configured to configure the virtual barrier based on user input. The system may further comprise a centralized monitoring station configured to display human-intelligible images based on the data from the one or more 3D motion sensors. The centralized monitoring station may be configured to receive an alert from the computerized communication system and, upon receipt of an alert, move the display of human-intelligible images to an alert display. The virtual barrier may be configured automatically by the computerized monitoring system. Upon detecting that the bounding box has touched or crossed the virtual barrier, the computerized monitoring system may be configured to confirm the crossing of the virtual barrier by skeletal tracking, blob tracking, or combinations thereof. The computerized monitoring system may be configured to use biometrics to identify the person.

In some aspects, this disclosure relates to non-transitory computer-readable media having embodied thereon instructions which, when executed by a computer processor, cause the processor to receive image data for a room from one or more 3D motion sensors, configure a virtual barrier within the room by a computerized monitoring system, classify an object within the room as a person, create a bounding box to circumscribe at least a portion of the person, and monitor a position of the bounding box over time and relative to the virtual barrier. The instructions may further cause the processor to accept user input to configure the virtual barrier. The instructions may further cause the processor to send an alert to a computerized communication system if the bounding box touches or crosses the virtual barrier. The instructions may further cause the processor to send another alert to the computerized communication system if all of the bounding box crosses the virtual barrier. The instructions may further cause the processor to send the image data to a centralized monitoring station.

The claimed invention may improve the function of the computer processor in analogous systems for monitoring patients by deploying new analytical models which require less processing speed and/or memory capacity than prior systems, while still allowing for the use of 3D data that can improve the accuracy of detection and reduce false alarms.

Additional objects, advantages, and novel features of this disclosure will be set forth in part in the description which follows, and in part will become apparent to those skilled in the art upon examination of the following, or may be learned by practice of this disclosure.

BRIEF DESCRIPTION OF THE SEVERAL VIEWS OF THE DRAWING

This disclosure references the attached drawing figures, wherein.

DETAILED DESCRIPTION

Figure 1:
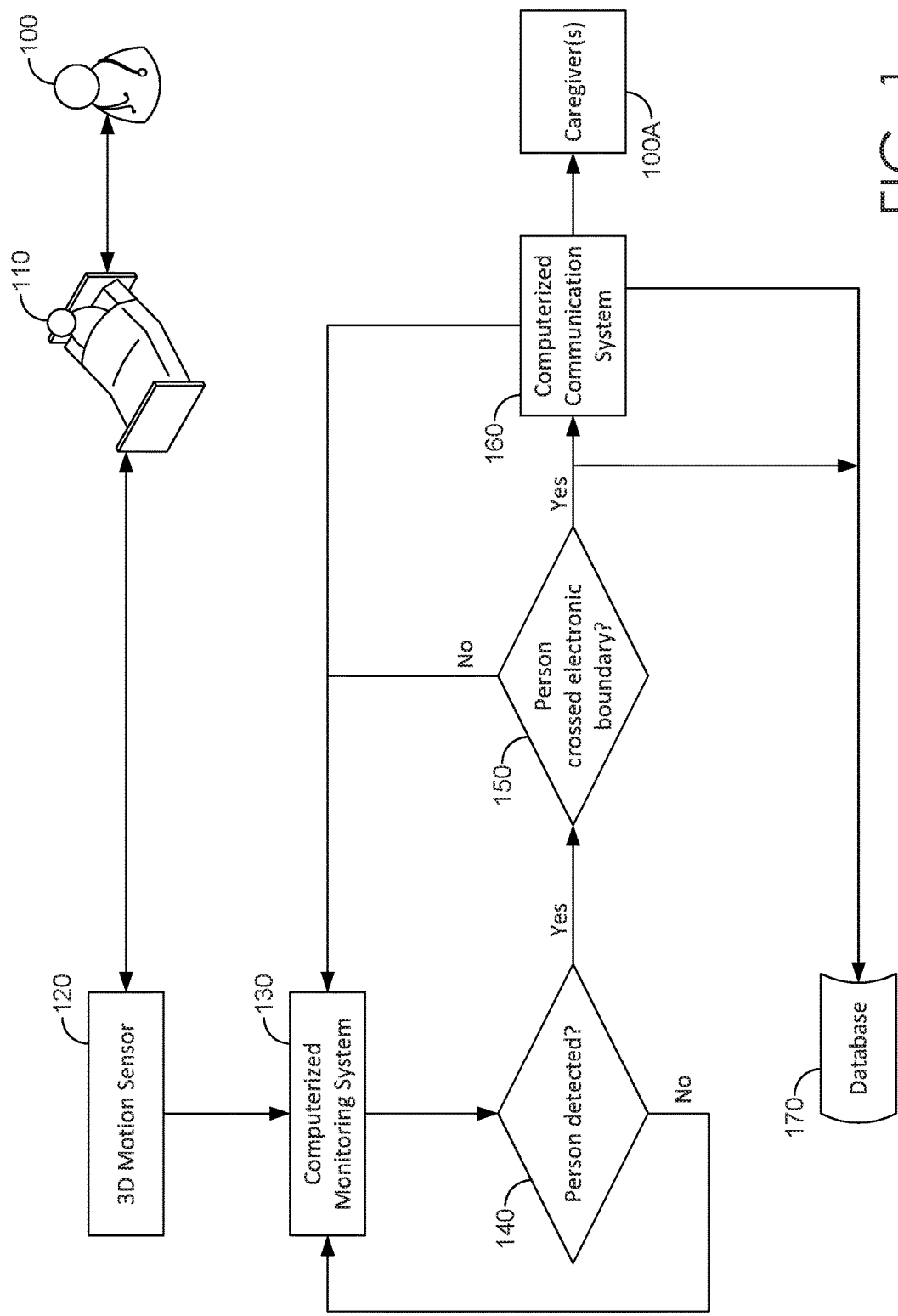
FIG. 1 is a schematic overview of an exemplary system and method for identifying the crossing of a virtual barrier, in accordance with aspects of this disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As used in this disclosure, a "patient" refers to a person being monitored, without regard to whether that person is under the immediate care of a medical professional, e.g., in a hospital, clinic, surgical center, outpatient diagnostic center, outpatient treatment center, rehabilitation facility, hospice care facility, assisted living facility, group home, private home, or other environment. As used in this disclosure, a "caregiver" may be a clinician, such as a doctor, nurse, physician's assistant, nurse's aide, orderly, physical therapist, and the like, or may be a paid or unpaid assistant who helps the patient with health care and/or tasks of daily living, such as a visiting nurse, a home health aide, a paid companion, a relative, a friend, or the like.

Patient movement may be monitored for a variety of reasons. Patients who are ill, disabled, or disoriented (e.g., because of injury or illness or as a side-effect of medication) may be more prone to fall than other people. Monitoring a fall-prone patient's movements can assist caregivers in providing prompt care to prevent a fall. For example, knowing when a patient is attempting to get out of bed would allow a caretaker to report quickly to the patient's bed and assist the patient to prevent a fall. Patients may, intentionally or unintentionally, disturb or damage medical equipment. For example, an uncomfortable or agitated patient may dislodge a nasogastral tube, or rub or pick at an intravenous line. These contacts can introduce germs from the patient's hands, displace medical equipment, damage medical equipment, and even cause personal harm. Knowing when a patient reaches for or is manipulating medical equipment may allow for early intervention, so that the equipment can be maintained as needed for the patient's safety, or adjusted in a manner that is safe for the patient and will not harm the equipment. As another example, it may be desirable to monitor when others approach a patient's bedside. For example, it may be desirable to evaluate the time that a caregiver spends with a patient, and whether the time in close proximity to the patient is consistent with certain medical needs, such as repositioning the patient as part of a bedsore prevention regimen.

Having a caregiver monitor a patient is not practical. Most caregivers—whether in a medical institution or in a home-care setting—have other responsibilities and cannot directly observe the patient 24 hours a day. Some monitoring systems may monitor the patient based on computer modeling of the patient and the patient's surroundings, such as the patient's bed. These systems are data-intensive, requiring in-room computer processing equipment or significant bandwidth to communicate data to maintain the 3D model over time. Also, systems which rely on modeling the patient and objects in the room with the patient, such as the patient's bed, may fail under common conditions, such as low-lighting, a patient covered by bedclothes, objects placed between the camera and the patient, etc.

The methods, systems, and computer-readable media disclosed herein provide for automated, computerized systems that can help identify the crossing of a virtual barrier. The virtual barrier can be flexibly set by a caregiver or other system user, to adapt to a variety of monitoring needs. The virtual barrier can also be set so as to detect behavior likely to result in an undesired outcome—such as a patient moving in a way that suggests the patient is trying to get out of bed—to allow time for a caregiver to intervene. The patient may be monitored using probability-based bounding boxes, which allow for image analysis that can identify a person or people in an image without further modeling, thereby reducing the data and processing capacity requirements for on-going monitoring. Alternately, probability-based bounding boxes can be used with more elaborate modeling, either as a back-up in case the primary modeling mode fails (e.g., because low lighting or obstructions deny the system data needed to update the model) or as a primary detection mode that can be verified against more elaborate modeling if a potential problem is detected.

An exemplary method and system for identifying the crossing of a virtual barrier are shown in FIG. 1. A 3D motion sensor 120 may be co-located with patient 110, who is tended by caregiver 100. For example, 3D motion sensor 120 may be located in or near a hospital room, bedroom, or other location where patient 110 spends a significant amount of time. The 3D motion sensor 120 may be positioned to have a view of most or all of the patient's body.

In general, the 3D motion sensor 120 is an electronic device that contains one or more cameras capable of identifying individual objects, people, and motion, regardless of lighting conditions. The 3D motion sensor 120 may further comprise one or more microphones to detect audio. As used in this disclosure, unless expressly described otherwise, reference to a sensor or sensors encompasses the singular and the plural, e.g., a singular sensor or an array of sensors, and an array of sensors may be physically housed in a unitary structure or may be physically distinct devices. The cameras may utilize technologies including, but not limited to, color RGB, CMOS sensors, infrared projectors, RF-modulated light, Time of Flight (ToF, including LIDAR), and combinations thereof. The 3D motion sensor may further contain one or more microprocessors and/or image sensors to detect and process information sent and/or received by the one or more cameras. Suitable 3D motion sensors can perceive depth, in contrast to 2D cameras which perceive only lateral and longitudinal positions. Exemplary 3D motion sensors include the Microsoft® Kinect® Camera, the Sony® Playstation® Camera, the Intel® RealSense® Camera, the Orbbec® Astra® Camera, the Orbbec® Persee® Camera, and the Asus® Xtion® Camera. Some of these exemplary 3D motion sensors include one or more microphones, although many aspects of the disclosure can be practiced without sensing audio. The 3D motion sensor may produce a depth map which is derived from ToF or comparable spatial analysis of the room, rather than pixel-based image analysis.

The 3D motion sensor 120 may be in electronic communication with a computerized monitoring system 130, either as a separate component of the same physical unit or device, or as separate devices. The 3D motion sensor 120 may be co-located with or remote from computerized monitoring system 130, so long as data can be sent by the 3D motion sensor 120 to the computer monitoring system 130 or retrieved by the computerized monitoring system 130 from the 3D motion sensor 120.

The 3D motion sensor 120 may operate continuously, or intermittently (for example, running for a fixed period at defined intervals), or on a trigger (e.g., when a motion detector or light sensor is activated, suggesting activity in the room). The 3D motion sensor 120 may operate continuously at all times while the monitoring is occurring, regardless of whether the person or object of interest is moving or not. The 3D motion sensor 120 may view the entire room or a large portion of the room by placement in a manner sufficient for the room to be visible to the camera. Alternately, the 3D motion sensor 120 may view any portion of the room that includes the patient or a portion of the patient to be monitored. The 3D motion sensor 120 may record video, or may forward video to the computerized monitoring system 130 or directly to a database, such as database 170, for storage. Video is a series of sequential, individual picture frames (e.g., 30 frames per second of video). The video data may include 3D depth data, data defining one or more bounding boxes, skeletal object tracking data and/or blob or object tracking data. In some implementations, it may be desirable for the sensors to capture video only, or sound only, or video and sound. Video only (with 3D depth data, bounding box data. skeletal object tracking data and/or blob or object tracking data) may make monitored patients more comfortable having conversations with visitors or caregivers than if sound is also captured. Alternatively, or additionally, to protect patient privacy and modesty, video displays of the image data from the 3D motion sensor may be blurred or pixelated or otherwise obscured, or the people and objects in the room may be converted from detailed image data to cartoons, less detailed drawings, or stick figures when displayed. The 3D motion sensor may collect and transmit data sufficient for measuring and analyzing movement and interaction between different people within the room, but transmit only sufficient image data for a partially obscured video, or a microprocessor associated with the 3D motion sensor and/or computerized monitoring station may process image and/or video data to make the individuals and/or details of the room or the activity of the room more difficult to distinctly identify. In some aspects, only 3D depth data, bounding box data, skeletal object tracking data and/or blob or object tracking data is transmitted, without video or still images.

With skeletal tracking alone, there can be factors affecting the cameras/image-video quality which affects the ability of the detection/monitoring system to detect a skeleton. Such factors, especially in a hospital, include, but are not limited to, sheets/blankets covering a patient, trays positioned over the bed hiding the patient and the patient blending into the bed and not having a skeleton recognized.

With blob detection alone, there can be an increase in false positives in detecting falls and "at risk" behavior. These false positives can occur because blob detection does not differentiate between types of 3D objects. Blankets, treys, caretakers, or other 3D objects can trigger an automated notification. Blob recognition also does not differentiate between parts of the body.

With bounding box detection, it may be difficult to fine-tune settings, such as confidence levels and thresholds for determining whether a boundary has been crossed, to achieve a balance between catching early movement toward a boundary and reducing false alarms, e.g., from a patient reaching for an object on a nearby table or nightstand. However, bounding box detection may require less data processing and/or may be computed more quickly than skeletal or blob detection.

Combinations of skeletal tracking, blob detection, and bounding box detection can overcome some of the drawbacks of using any individual approach. If a skeletal tracking system is unable to track a skeleton, then a virtual blob detection system and/or bounding box detection system may be used to capture and/or recognize movement. If a virtual blob detection system and/or bounding box detection system has insufficient specificity to avoid false alarms at a rate unacceptable to a given user, skeletal tracking can be selectively used to confirm or clarify determinations made initially by virtual blob detection and/or bounding box detection. All three systems could be run simultaneously, or one system could be run preferentially to the other two, or one system could be run routinely with one or both of the other systems run to confirm potential detections.

The computerized monitoring system 130 may receive and analyze data from 3D motion sensor 120. The computerized monitoring system 130 and/or the 3D motion sensor 120 may be configured to monitor and/or analyze only a portion of the full view of the 3D motion sensor 120. For example, 3D motion sensor might be capable of viewing most or all of a room, or a room and part of an adjacent hallway. However, to reduce processing capacity and communication bandwidth requirements, the 3D motion sensor 120 may be configured to capture data from a limited view, and/or the computerized monitoring system 130 may be configured to analyze only a portion of the data from 3D motion sensor 120. For example, the computerized monitoring system 130 may analyze data from a pre-defined area around a patient, or around a patient's bed or chair.

Computerized monitoring system 130 is specifically designed and programmed to monitor activity based on information received from 3D motion sensor 120. Computerized monitoring system 130 may use image classification (e.g., identification of an "object" as a person), facial recognition, height, distance between body points, and/or other biometrics (e.g., iris scanning, fingerprints, etc.) to "lock onto" the patient for analysis, helping to avoid the possibility of the computerized monitoring system 130 tracking a visitor or caregiver who might pass between the patient and the 3D motion sensor, or others who may enter the 3D motion sensor's field of view. Computerized monitoring system 130 may use facial recognition, height, distance between body points, etc. to identify one or more caregivers for the patient, distinct from the features of the patient. Alternately, or in addition, 3D motion sensors and/or additional sensors, such as an RFID reader, may read an electronic receiver, transmitter, or transceiver associated with the patient and/or with a caregiver to identify and/or distinguish individuals in the room. The patient and/or the caregiver may wear, carry, or otherwise be associated with such a transceiver in the form of a badge, token, bracelet, cell phone, or other device. As one example, the patient may wear, carry, or otherwise be associated with a transmitter and the caregiver may wear, carry, or otherwise be associated with a receiver. Alternately, the patient may wear, carry, or otherwise be associated with a receiver and the caregiver may wear, carry, or otherwise be associated with a transmitter. Or both the patient and the caregiver may wear, carry, or otherwise be associated with a transmitter or a receiver or both.

Alternately, or additionally, the patient, the caregiver, or both may be associated with a bar code, words, QR code, or other visual symbol or identifier, for example, on an ID badge or bracelet. The 3D motion sensor 120 and/or the computerized monitoring system 130 may note the barcode, words, QR code, or other visual symbol or identifier, which could later be compared to a database to identify the patient or caregiver, or the 3D motion sensor 120 and/or the computerized monitoring system 130 could be given access to a database and configured to determine the identity of the patient and/or caregiver using the visual symbol or identifier. A person may be inferred to be a caregiver by identification of clothing such as scrubs, a hospital uniform, a lab coat, etc., in contrast to a hospital gown, nightgown, or street clothes. Similarly, a person in a hospital gown or nightgown may be inferred to be the patient. In a home or home-like environment, street clothes may be associated with the caregiver, while in a hospital or institutional environment, street clothes may be associated with a visitor.

If desired, the system might not distinguish individuals, or might not seek to distinguish individuals outside of particular circumstances. For example, the system may seek to confirm the identity of the patient and/or a caregiver upon system start-up, upon detection of a potential problem, upon any event that would trigger the system to send data to the patient's electronic health record, after specified time intervals during monitoring, after random time intervals during monitoring, or combinations thereof.

The computerized monitoring system 130 may analyze data from 3D motion sensor 120 to determine whether a person is detected, shown as step 140 in FIG. 1. The computerized monitoring system may analyze image data, depth data, or both, to evaluate whether any "objects" in the room appear to be a person. For example, 2D RGB video can be used to identify a person, as can 3D data, such as an IR depth map, ToF data, or stereo vision from two or more 2D RGB cameras. A probability-based bounding box may be shown around the object that is determined to be a person, using a predetermined threshold for the confidence that the object is a person. The bounding box may circumscribe the entire person (a full-body bounding box), or the bounding box may circumscribe only a portion of the person, such as the upper body, lower body, face, etc. One of skill in the art will appreciate that image classifier systems can analyze images and predict with a degree of confidence whether an object within an image fits a certain class, such as "person." Accordingly, the system may look for objects that are likely to be a person with at least 50% confidence, or at least 75% confidence. Using a higher confidence interval may lead to the system treating the room as unoccupied an unacceptable number of times when there is, in fact, a person in the room. The acceptable limits for failing to detect a person will, of course, depend on the purpose of the monitoring and the risk tolerance of the monitoring person or organization. Similarly, the system may calculate a box around the object likely to be a person based on the desired confidence that the box circumscribes the entire person, or the entirety of the person in view of the camera, or the desired portion of the person, or an acceptable portion of the person or portion of the person (e.g., most of the upper body, most of the face, etc.). The confidence level for circumscribing the entire person or portion of the person can be set based on the tolerance of the system user for error. For example, if it is critical that a patient not leave bed unassisted, the tolerance for underestimating the extent of the patient may be very low, because a smaller box would underestimate the risk that the patient has actually left the bed. Conversely, if the tolerance for overestimating the extent of the patient is high, the system may frequently notify a caregiver of an undesired event when no such event has occurred or is likely to occur.

Figure 8:
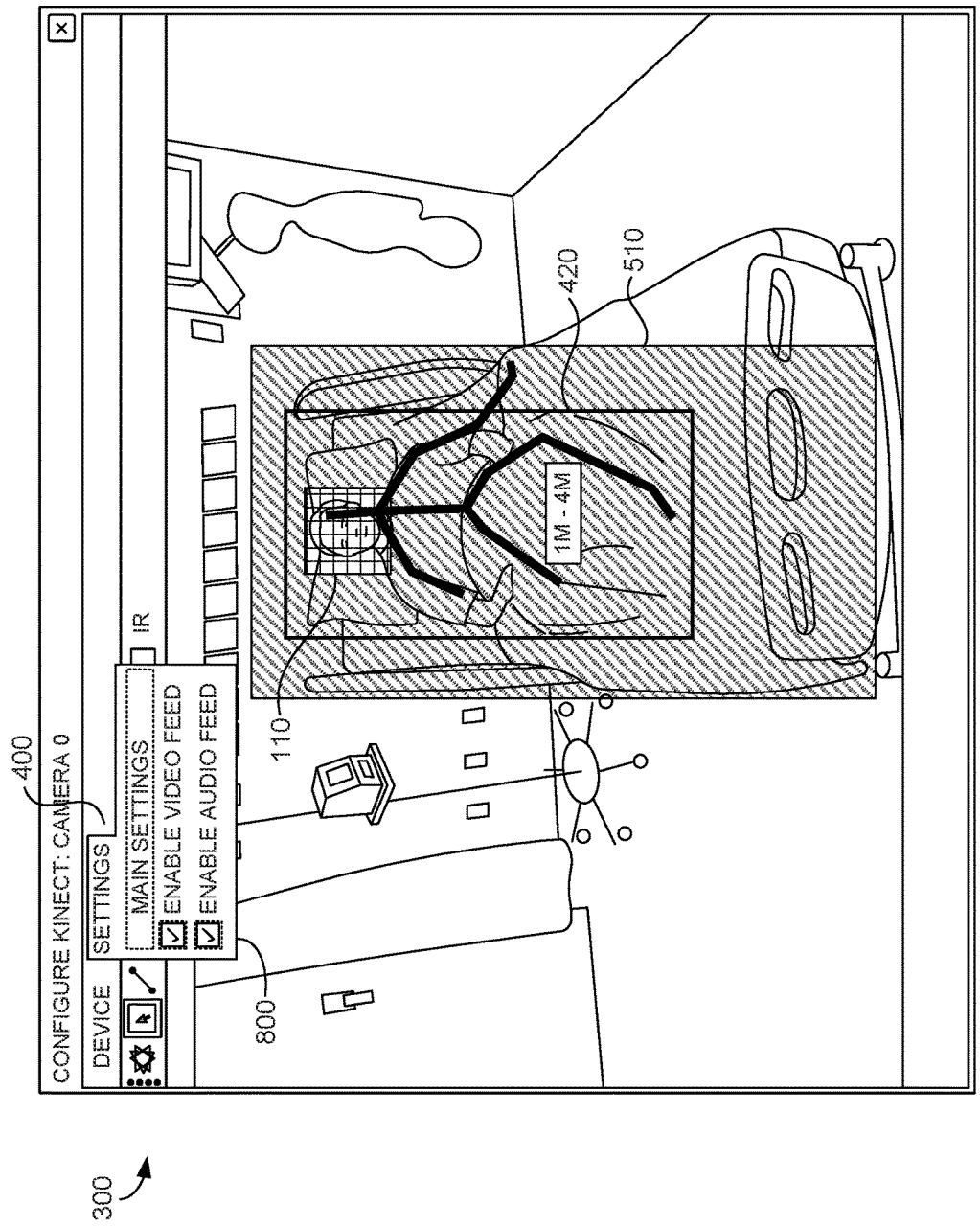
FIG. 8 is a view of an exemplary centralized monitoring primary display, in accordance with aspects of this disclosure.
Figure 9:
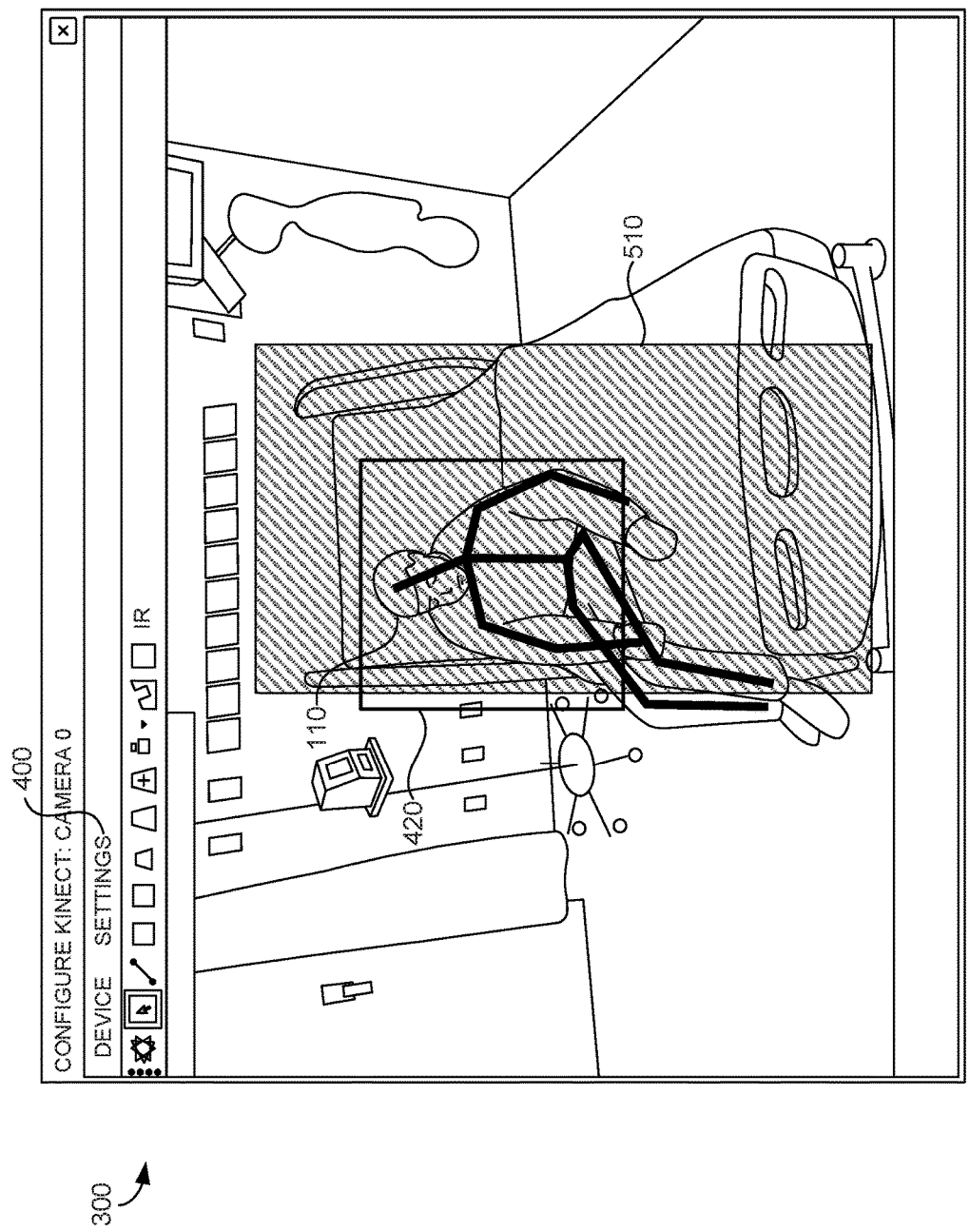
FIG. 9 is a view of an exemplary centralized monitoring primary display, in accordance with aspects of this disclosure.

If a person is identified, the computerized monitoring system 130 may determine whether the person has crossed an electronic boundary 150. A human-intelligible display as shown in FIGS. 8-9 illustrates this. In each of FIGS. 8 and 9, a patient 110 is partially noted by a bounding box 420. If patient 110 sits up and begins to move out of the bed, the bounding box 110 shifts outside the electronic boundary defined by box 510. Returning to FIG. 1, if no person is detected, or if the person (as represented by a bounding box 420) has not crossed the virtual barrier 510, the computerized monitoring system continues to monitor for a person and/or a boundary crossing. If a person has crossed the virtual barrier, an alert is sent to a computerized communication system 160. An alert may be sent only if a specified minimum portion of the bounding box 420 has crossed the virtual barrier 510.

To assess the patient's position, in addition to or as an alternative to the use of a bounding box, computerized monitoring system 130 may use skeletal tracking, blob tracking, or other image recognition techniques to identify one or more tracking points on the patient's body, such as hips, shoulders, knees, chin, nose, etc. The patient's position can then be analyzed by tracking skeletal segments, or the shape and orientation of a blob, or specified tracking points. For example, the system may identify or infer the position of the patient's right knee at a time designated as T1, as by the coordinates (x1, y1, z1) of the patient's right knee in a picture frame. At a later time T2, the patient's right knee might be at coordinates (x2, y2, z2). Based on this information, motion, speed and direction of movement (or lack of movement) can be derived utilizing the elapsed time and comparing the two 3D coordinates. As opposed to conventional motion sensors, which use captured motion to control a camera, the 3D motion sensor used in the methods and systems described herein is used to compute the motion. Further, a 3D motion sensor, as opposed to a 2D motion sensor, offers depth sensitivity that can help to reduce false alarms (e.g., by identifying rotational or vertical movement, as might occur when a patient rolls to or from one side of the body), as well as help to isolate the analysis to the patient and avoid false alarms or false confirmations of repositioning from other objects or individuals who might pass in front of or behind the patient.

Skeletal and/or blob tracking may be used under certain circumstances to supplement the use of a bounding box. For example, skeletal and/or blob tracking may be used to confirm an initial detection that a virtual barrier has been crossed. The skeletal and/or blob tracking may be automatically turned on by the computerized monitoring system 130 on detection of the crossing of a virtual barrier using bounding boxes, or a human user may have the option to turn on skeletal and/or blob tracking, e.g., if a number of false alerts have been generated for a particular patient. Alternately, skeletal and/or blob tracking may be preferentially used for new patients or patients with a history of wandering off or disrupting medical equipment, and bounding boxes may turn on if the monitoring does not detect any crossing of the virtual barrier for a given time period, such as 24 hours or 48 hours. In this way, the relatively lower data processing and transmission requirements of the bounding box method can be used when the risk of a problem is somewhat lower, and more data-intensive individual tracking methods can be used when the risk of a problem is somewhat higher or when the bounding box method is producing an unacceptable number of false alerts. False alerts may be associated with active patients, active rooms (e.g., many visitors or much activity in the room), or relatively large patients, whose bounding boxes may take up a relatively greater proportion of the area within the virtual barrier. Of course, false alerts using the bounding boxes can also be reduced by modifying the confidence levels that the object being tracked is a person or that the person is circumscribed within the bounding box, with higher confidence levels tending to cause fewer false alerts, or by requiring a minimum portion of the bounding box, greater than 0%, to cross the virtual barrier before an alarm is sent.

If more than one detection technique or system is used (skeletal tracking, blob tracking and/or bounding box tracking), an alert may be sent if any method detects that the virtual barrier has been touched or crossed, or an alert may be sent only if two or more of the methods agree that the virtual barrier has been touched or crossed, or an alert may specify which method(s) detected the virtual barrier has been touched or crossed and/or whether an alternate method could not confirm that the virtual barrier has been touched or crossed and, if desired, which alternative method could not make the confirmation.

If a person or the specified minimum portion of the bounding box representing the person has crossed the virtual boundary, computerized monitoring system 130 may send an alert to computerized communication system 160. On receiving an alert from computerized monitoring system 130, computerized communication system 160 may send a human-intelligible signal or request for attention. For example, computerized communication system 160 may send an alert to an amplifying speaker, public announcement system, television, monitor, mobile phone, computer, pager, or other display device in a patient's room. The alert, which could be audible or visible or both, may request that the patient return to their prior position. For example, if the virtual barrier is set to detect when a patient is trying to get out of bed, the alert may request that the patient return to bed and wait for assistance. The alert could be text, sound, or video, or could consist of flashing lights in the room or on a display, or another visible change in the patient's room, such as a change in the color of a border of a monitor or television, or a change in the brightness or color of the light in the room. The alert could take the form of an automated phone call, voice mail message, e-mail message, SMS message, or the like. Alerts to the patient may be disabled, for example, if the patient is known or believed to be unable or unwilling to respond. For example, if a patient has a history of seizures or other involuntary movement, an alert to the patient may be unhelpful.

In addition to or instead of alerting the patient, computerized communication system 160 may alert one or more caregivers 100A. As with alerts intended for a patient, alerts for a caregiver could be audible or visible or both, and may include text alerts, instructions, or other signals that something is amiss, e.g., flashing lights, color schemes, etc. An alert for a caregiver may be sent to the patient's room, or may be sent to a device carried by the caregiver, such as a cell phone or pager, or may be sent to a nursing station or dispatch center. An alert for a caregiver may be sent to a primary caregiver, and, if no change is detected within a predetermined response time, an alert may be sent to one or more additional caregivers. Alternately, an alert may be sent to two or more caregivers at the outset. Alerts may also be sent to others who might not have primary responsibility for the care of the patient, such as family members or guardians. Alerts, possibly including the 3D motion sensor data in the time period before the alert and/or any response(s) to the alert, may be recorded, for example, in database 170. Database 170 may include, or may provide information to, or may be accessible by, an Electronic Health Record (EHR) for one or more patients. In this way, alerts and responses may be recorded automatically in an EHR without caregiver input. Exemplary responses to an alert may include a human operator cancellation of the alert (e.g., based on a caregiver or centralized monitoring station attendant confirmation that the patient is safe or has returned within the virtual boundary), a system determination that the patient has returned within the virtual boundary, or a system determination that a second person has entered the virtual boundary (presumably a caregiver or clinician tending to the patient). If desired, the computerized monitoring system may identify individuals before clearing an alert, to confirm that the second person crossing the virtual boundary is a caregiver or clinician, or even to document the identity of the individual responding to the alert.

A confirmation that an alert has been resolved—because the patient returned within the virtual barrier or because a caregiver or clinician has response—may be communicated to a patient, a caregiver and/or others, in any of the modes and manners described for alerts. A confirmation that an alert was resolved may also be recorded in database 170, an EHR, or in any other desired file or storage location.

Figure 2:
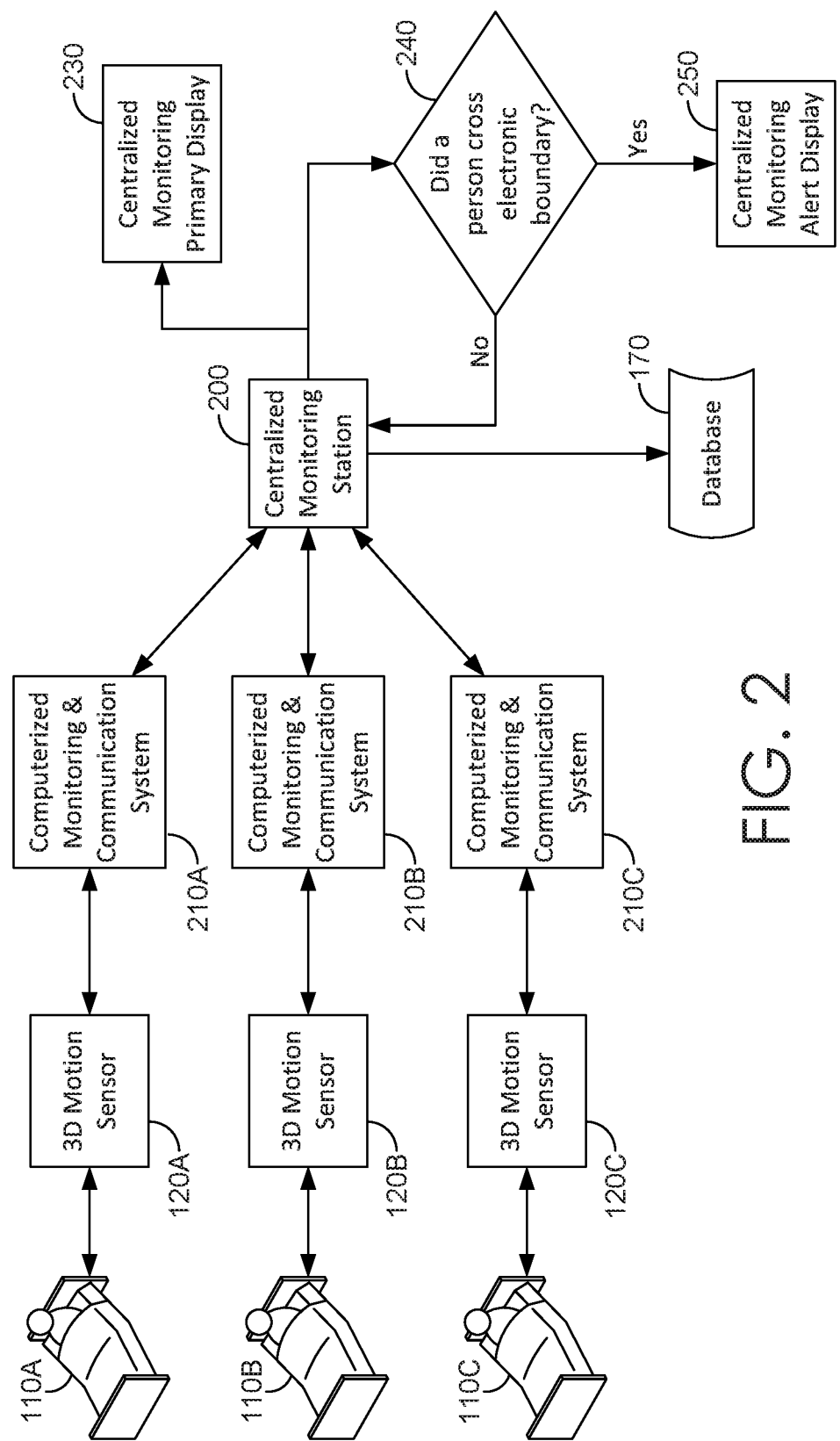
FIG. 2 is a schematic overview of an exemplary system and method for centralized monitoring, in accordance with aspects of this disclosure.

Computerized monitoring system 130 and/or computerized communication system 160, shown in FIG. 2 as combined computerized monitoring and communication systems 210A, 210B, and 210C, may also be in communication with a centralized monitoring station 200. A centralized monitoring station 200 may be used with a single 3D motion sensor 120 for a single patient. For example, centralized monitoring station 200 may include a display in a home of a family member or guardian of patient 110. As shown in FIG. 2, a plurality of 3D motion sensors 120A, 120B, and 120C may monitor a plurality of patients, 110A, 110B, and 110C, respectively. The 3D motion sensors 120A, 120B, and 120C may be monitored by distinct computerized monitoring and communication systems 210A, 210B, and 210C, respectively. Alternatively, 3D motion sensors 120A, 120B, and 120C could each send 3D motion and/or sound data to a single computerized monitoring system 130 or to a single combined computerized monitoring and communication system.

The computerized monitoring system 130 and/or computerized monitoring and communication systems 210A, 210B, and 210C may send filtered or unfiltered data, such as images and/or a live video feed, with or without sound, from 3D motion sensors 120A, 120B, and 120C to centralized monitoring station 200. The 3D motion sensor data may be received and displayed as human-intelligible images on a centralized monitoring primary display 230, which may be a single display monitor or a series or grid of two or more display monitors. As mentioned above, the computerized monitoring system and/or the centralized monitoring station may apply filters before the 3D motion sensor data is displayed, for example, to blur or pixelate the face or body of the patient, to protect patient privacy. In addition, video and/or sound, if sound is provided, can be turned off at any node, including centralized monitoring primary display 230 and directly at the 3D motion sensor, to protect patient privacy, e.g., while the patient is receiving visitors, bathing, changing clothes, etc. If a large number of patients are being monitored at the same time, the centralized monitoring primary display 230 may be enlarged so that it can aggregate multiple telemetry feeds, or more than one centralized monitoring station primary display 230 could be used. Regardless of whether the data is filtered or unfiltered, it may still be processed by the computerized monitoring system 130, a computerized monitoring and communication system (e.g., 210A, 210B, or 210C) and/or the centralized monitoring station 200 to render the data as a human-intelligible visual image or series of images (e.g., video).

When the computerized communication system receives an alert, the computerized communication system may send the alert to the centralized monitoring station 200. At step 240, on receipt of a determination from the computerized monitoring system 130 and/or an alert from the computerized communication system 160 for a particular 3D motion sensor, the display from that sensor may be moved from centralized monitoring station primary display 230 to centralized monitoring station alert display 250 or duplicated on centralized monitoring station alert display 250. Centralized monitoring station alert display 250 may be a subset of the display or displays of centralized monitoring station primary display 230, or may be a distinct display or series of displays. If live video is available but was not being displayed on centralized monitoring station primary display 230, the live video may be displayed on centralized monitoring station alert display 250 after an alert is received. Centralized monitoring station alert display 250, or an attendant there, may analyze the video feed to determine what is happening in the patient's room. If a caregiver has arrived and is tending to the patient or otherwise correcting the cause of the alert, the centralized monitoring station alert display 250 or attendant may clear the alert. If an alert has been sent to a caregiver and no response is detected or received, centralized monitoring station alert display 250 or an attendant may notify an alternate or back-up caregiver that the patient needs assistance. Alerts and any actions taken or responses received or observed at centralized monitoring station 200 may be recorded, for example, to database 170.

The centralized monitoring station primary display 230 may routinely display live video for monitored patients. An attendant at the centralized monitoring station primary display 230 can use the live video feed to detect other problems, such as a patient fall, a patient gesture that he or she needs assistance, an unauthorized person has entered the patient's room, etc.

The various system components and/or method steps may be situated and/or performed remotely from one another. So long as the components can transfer data and perform the functions described, the components or any subcombination of components could be located together, even, in some aspects, in a singular physical housing. Alternately, the components or any subcombination of components could be remote from one another, either in different rooms, different floors of a building, different buildings, different cities, or even different countries or continents. The centralized monitoring station 200, for example, may reside at a nursing station on the same floor or on a different floor of the same building as the 3D motion sensor, or could be in a regional center that receives telemetry from a plurality of 3D motion sensors in different rooms, buildings, or even cities, and possibly in a variety of patient environments. That is, a computerized monitoring system, computerized communication system and/or centralized monitoring station may process data from 3D motion sensors in hospitals, outpatient centers, assisted living facilities, and/or private homes, or may be specific, e.g., to a particular patient or healthcare organization (such as a hospital or hospital network).

Figure 3:
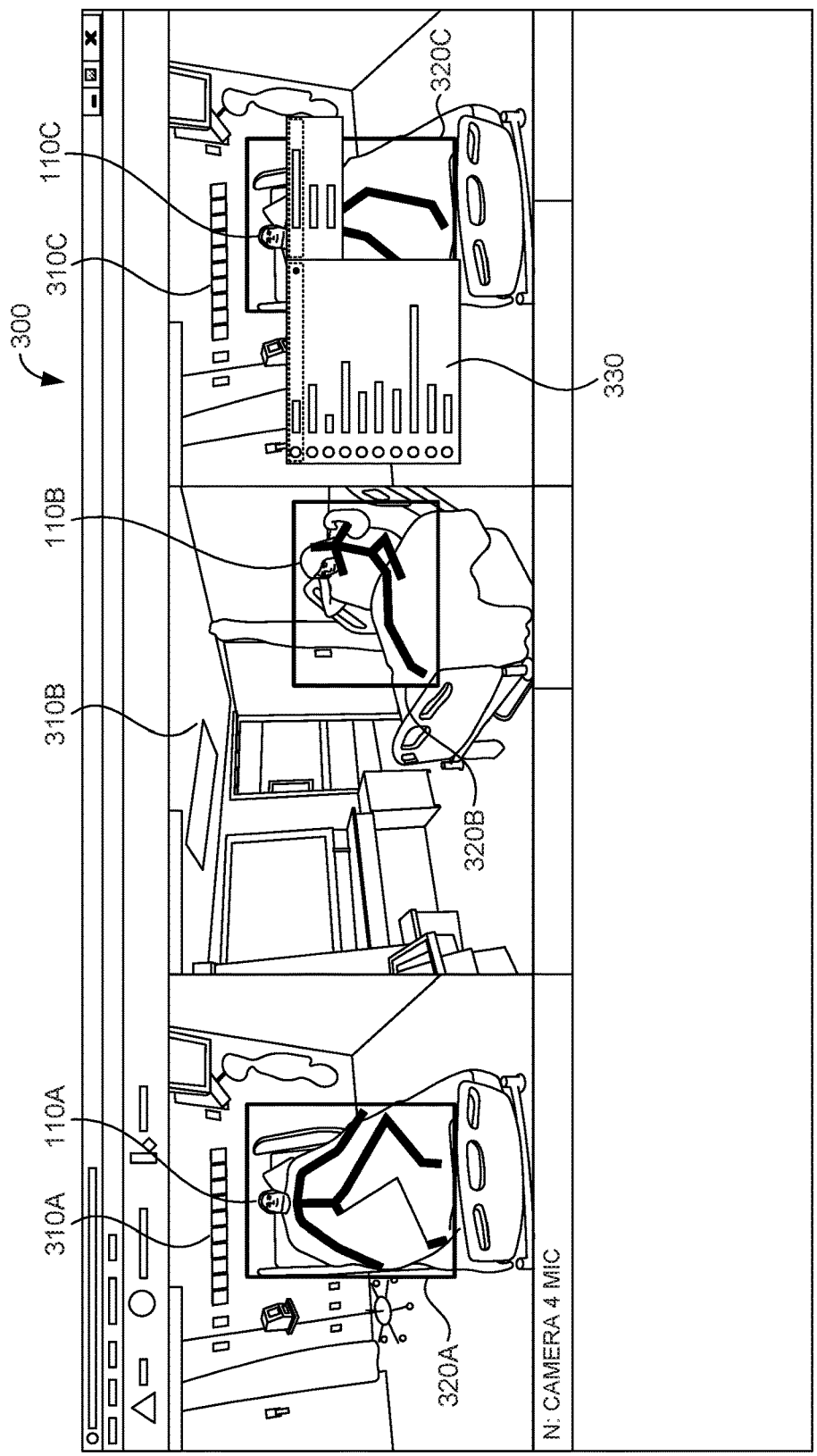
FIG. 3 is a view of an exemplary centralized monitoring primary display, in accordance with aspects of this disclosure.

The computerized monitoring system and/or centralized monitoring station may allow a user to configure a virtual barrier or boundary around a patient or a location where the patient spends time, such as a bed, chair, chaise, etc. FIG. 3 shows an exemplary display 300 of visual telemetry data for multiple patients 110A, 110B, and 110C, in simultaneous views 310A, 310B, and 310C, respectively, as might be configured on centralized monitoring station primary display 230. As shown, views 310A, 310B, and 310C appear on a split screen, however, different views could also be shown on separate displays. In addition to showing patients 110A, 110B, and 110C, display 300 shows bounding boxes 320A, 320B, and 320C for each patient. It will be appreciated that although FIGS. 3-9 show a skeleton figure within each of the bounding boxes 320A, 320B, and 320C, the bounding boxes could be used without any additional tracking means, or any other suitable means of tracking the patient's body position could be used, including, without limitation, blob tracking, object tracking, or other image recognition techniques to identify one or more specific tracking points on the patient's body, such as the patients hip(s), shoulder(s), knee(s), chin, nose, etc. The bounding boxes 320A, 320B and 320C are of slightly different shapes and orientations, although each of the bounding boxes circumscribes most or all of the person being monitored. The bounding boxes need not encompass the entire person, and the bounding boxes need not have the same extent settings (e.g., full-body, upper-body, lower-body, face, etc.) for each person being monitored. As such, the bounding boxes 320A, 320B, 320C could have more pronounced differences in shape, size and orientation than shown in FIG. 3. In addition, view 310C shows a pop-up menu 330, which may present configuration options for view 310C or options for responding to an alarm associated with monitored patient 110C or both.

Figure 4:
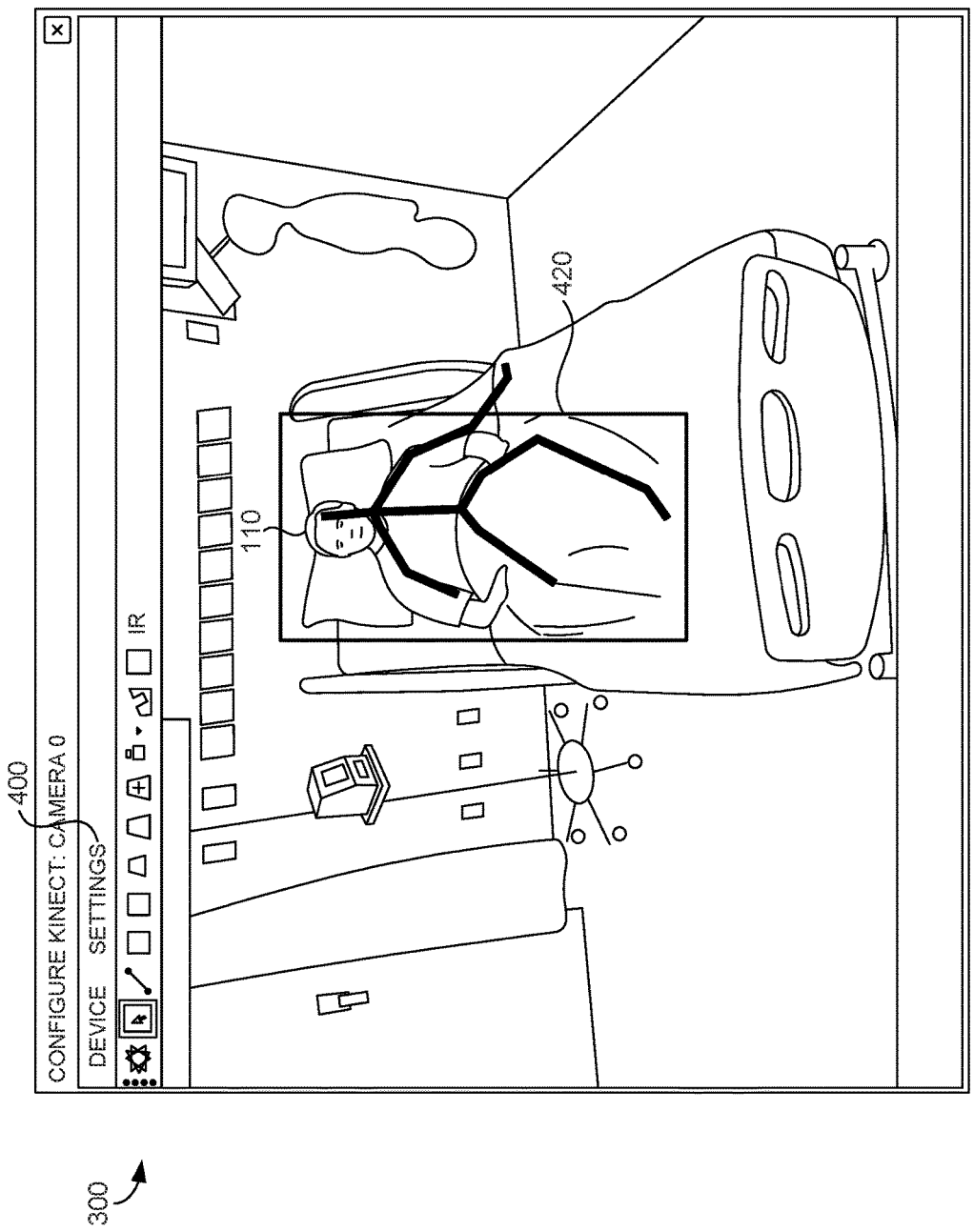
FIG. 4 is a view of an exemplary centralized monitoring primary display, in accordance with aspects of this disclosure.
Figure 5:
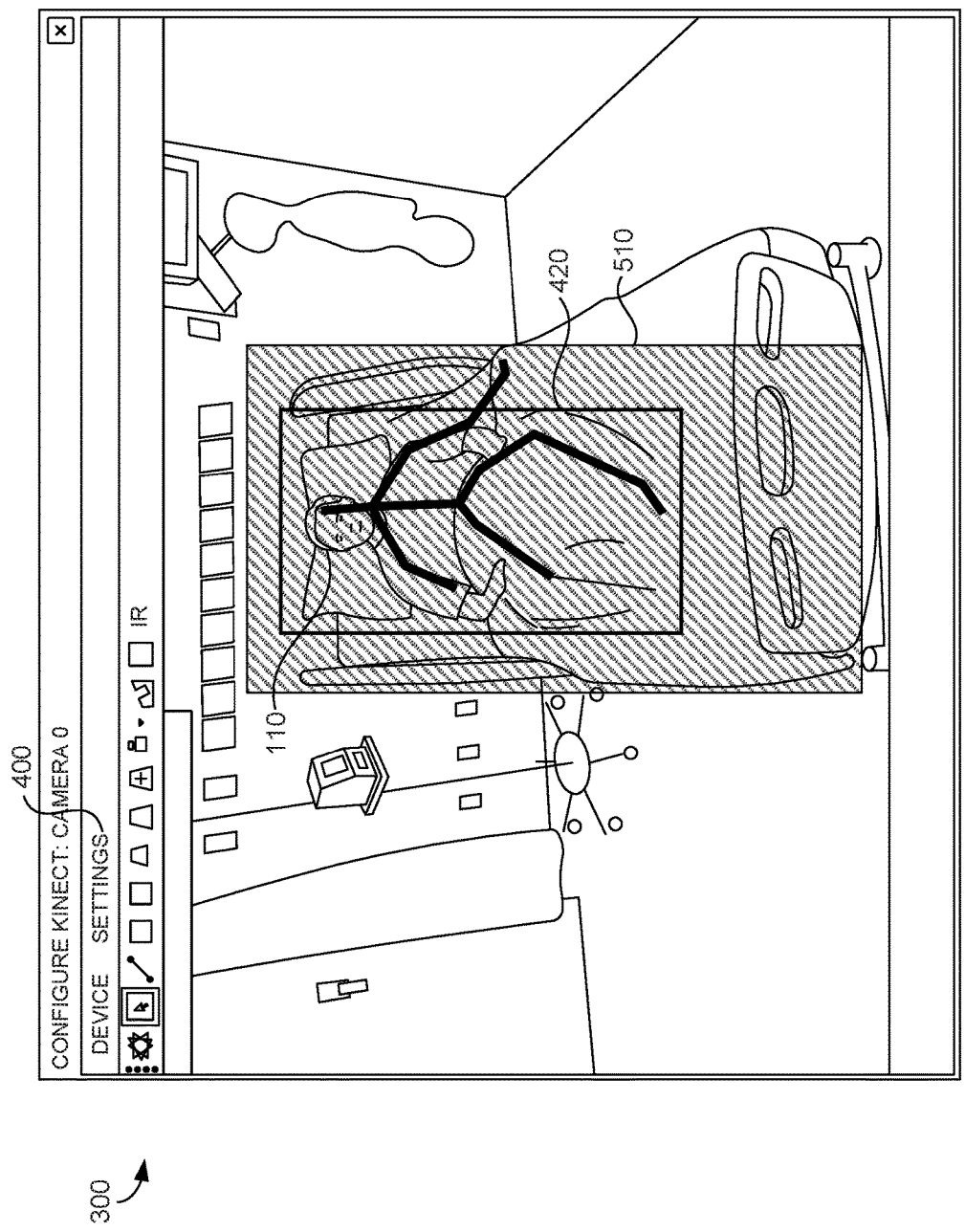
FIG. 5 is a view of an exemplary centralized monitoring primary display, in accordance with aspects of this disclosure.

FIG. 4 shows an exemplary display 300 of visual telemetry data for a single patient 110, with bounding box 420 and menu 400. FIG. 5 shows the same exemplary display 300 as FIG. 4 after a user has selected a menu option to define and/or confirm a virtual barrier 510. The virtual barrier 510 may be automatically generated by the computerized monitoring system 130. For example, computerized monitoring system 130 may define a virtual barrier 510 by outlining the perimeter or silhouette of an object, such as a bed or chair, or a line, for example across the threshold of a door. Virtual barrier 510 is shown as rectangular, but virtual barrier could be any closed figure, such as an oval, circle, square, hexagon, etc., or could be a line, arc, or open figure, such as a zig-zag line or semi-circle.

Analysis of image data may be limited to the virtual barrier 510 and bounding box 420, to reduce the processing capacity required to perform the analysis. If image data is transferred between remote system components, only data from the virtual barrier 510 and bounding box 410 may be routinely transferred, to reduce bandwidth and storage capacities required for the system's operation. In some aspects, the system may be configurable to analyze, transmit, and/or store all data within the field of view of the 3D motion sensor, either routinely or on the occurrence of a specified event, such as an alert.

Figure 6:
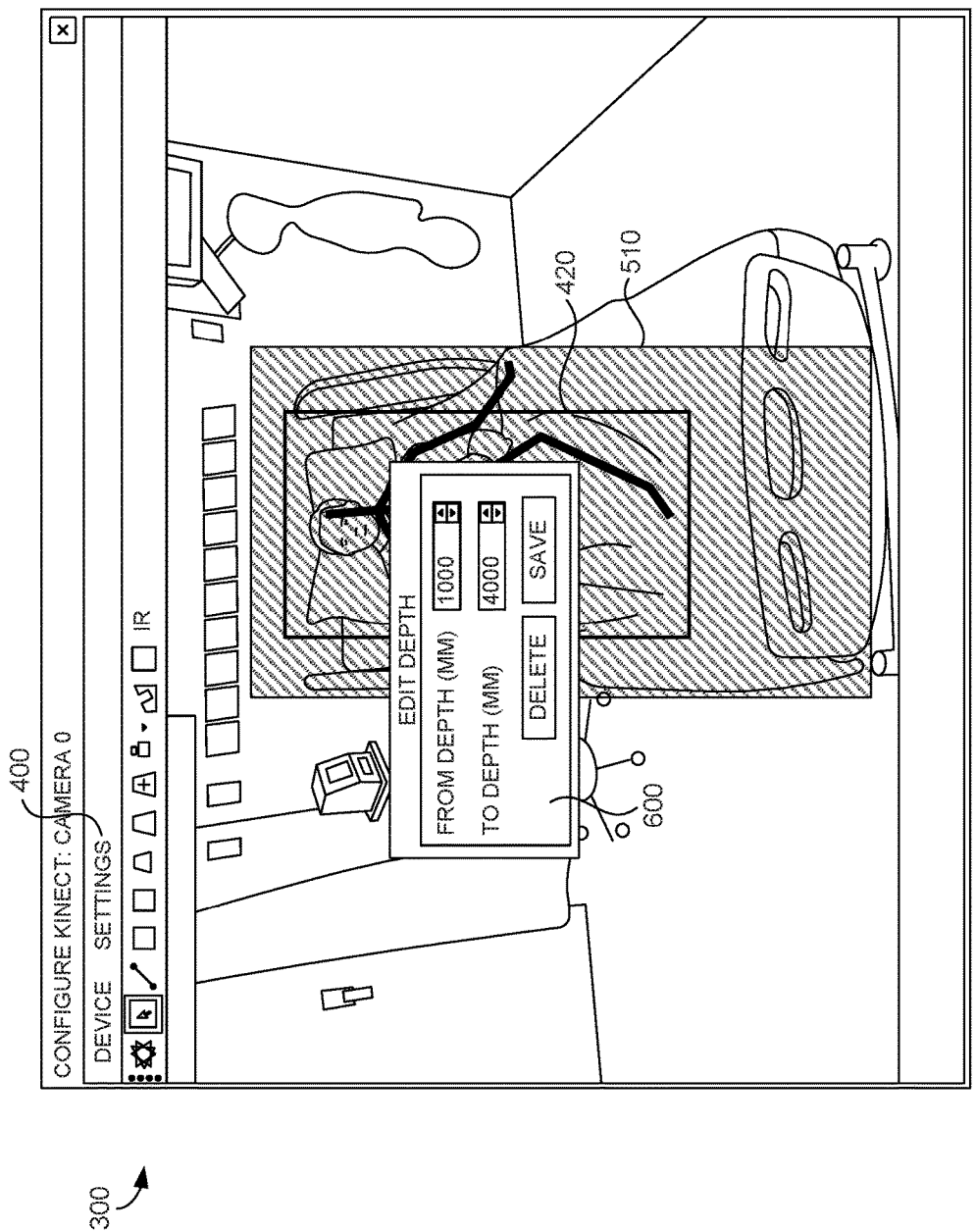
FIG. 6 is a view of an exemplary centralized monitoring primary display, in accordance with aspects of this disclosure.

As shown in FIG. 6, the virtual barrier 510 may have a third dimension of depth, e.g., be defined as a volume. The depth of the virtual barrier 510 may be automatically generated by the computerized monitoring system 130. By selecting a configuration option from menu 400, a user may alter or reset the depth that defines virtual barrier 510 using a pop-up menu 600. Alternately, the extent, placement and/or depth of virtual barrier 510 may be determined entirely by a system user, such as by entering coordinates or distances, as shown in pop-up menu 600 in FIG. 6, or by providing selection tools like drag-and-drop and pull-to-expand boxes or other shapes or tools.

Figure 7:
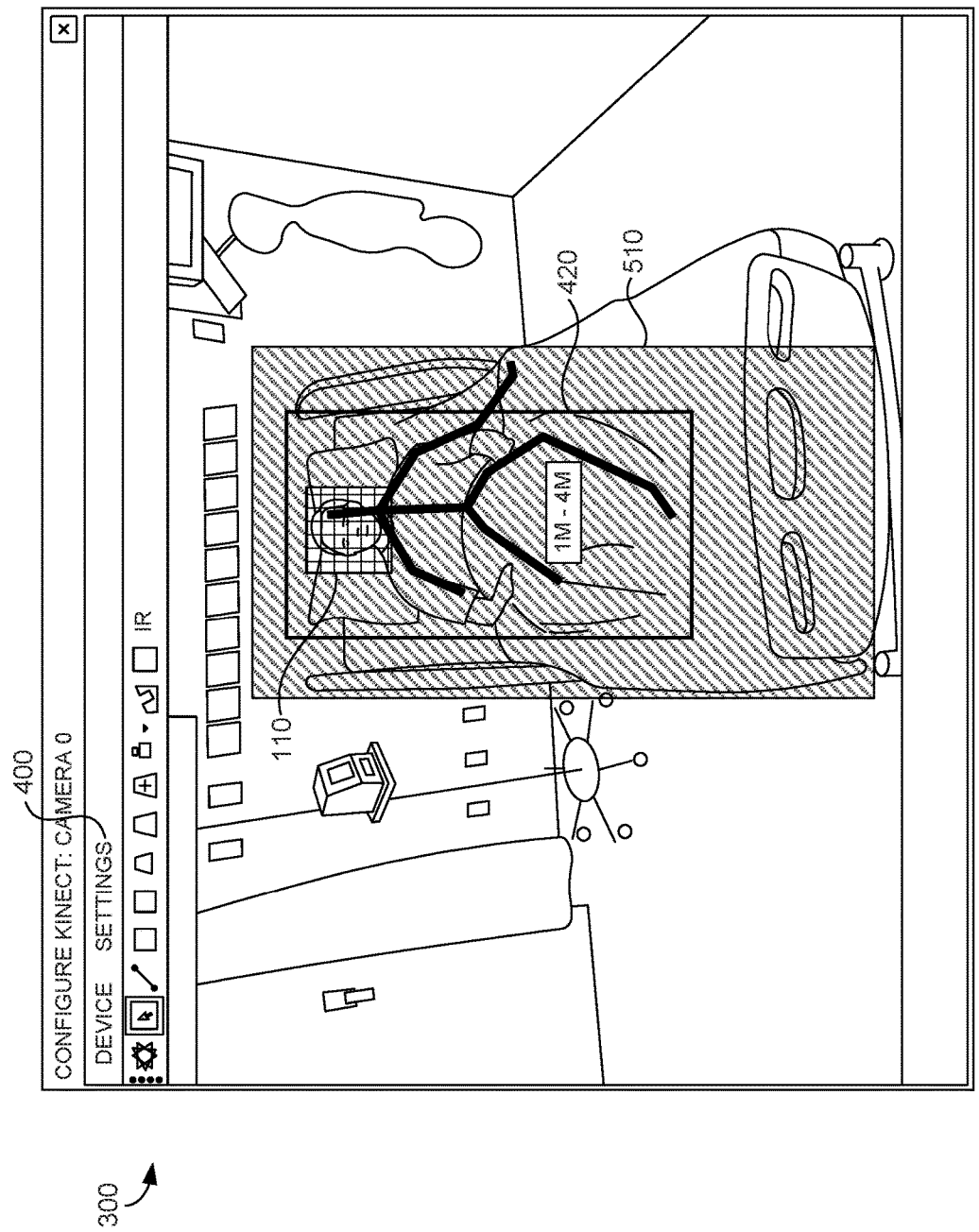
FIG. 7 is a view of an exemplary centralized monitoring primary display, in accordance with aspects of this disclosure.

FIG. 7 shows a configured virtual barrier 510 overlaid on visual telemetry for a monitored individual 110, surrounded by bounding box 420. FIG. 8 shows additional configuration options 800 from menu 400, allowing a user to select whether to display video telemetry ("VIDEO FEED"), audio telemetry ("AUDIO FEED"), or both. FIG. 9 shows patient 110 moving to the side of the bed. As the patient moves, so does bounding box 420. When bounding box 420 moves beyond virtual barrier 510, as shown in FIG. 9, computerized monitoring system 130 detects the crossing of the virtual barrier 510 by the bounding box 420 and issues an alert.

Computerized monitoring system 130 may determine that the bounding box 420 has crossed the virtual barrier 510 only if a minimum portion of the bounding box 420 has crossed the virtual barrier 510. Portions of the bounding box 420 can be measured, for example, as a percentage of the pixel area of the bounding box, a minimum number of pixels within the bounding box, or a percentage of the volume of the bounding box. Measuring a percentage of the volume of the bounding box requires using a depth parameter for the bounding box, however, even if a depth parameter is used, a 3D bounding box may still be evaluated for crossing the virtual barrier based on pixel area or number of pixels. The portion of the bounding box 420 that must cross the virtual barrier 510 to trigger an alarm can be set at any desired level, such as at least 0% of the pixel area or volume of the bounding box (zero percent, e.g., if the bounding box touches but does not cross the virtual barrier), at least 10% of the pixel area or volume of the bounding box, at least 20% of the pixel area or volume of the bounding box, or at least 30% of the pixel area or volume of the bounding box. It will be appreciated that setting the threshold for an alarm to a smaller percentage or number of pixels will result in alarms based on less movement by the person being monitored, with a potentially higher number of alarms, and setting the threshold for an alarm to a larger percentage or number of pixels will result in alarms only with greater movement by the person being monitored toward the virtual barrier, with a potentially lower number of alarms. In this way, setting a minimum portion of the bounding box that must cross the virtual barrier to trigger an alarm is a way to adjust the sensitivity of the detection method, and potentially to reduce false alarms (increasing the minimum portion of the bounding box that must cross the virtual barrier to trigger an alarm) or to trigger an alarm more quickly upon detection of possible intent to cross the virtual barrier (decreasing the minimum portion of the bounding box that must cross the virtual barrier to trigger an alarm).

Figure 10:
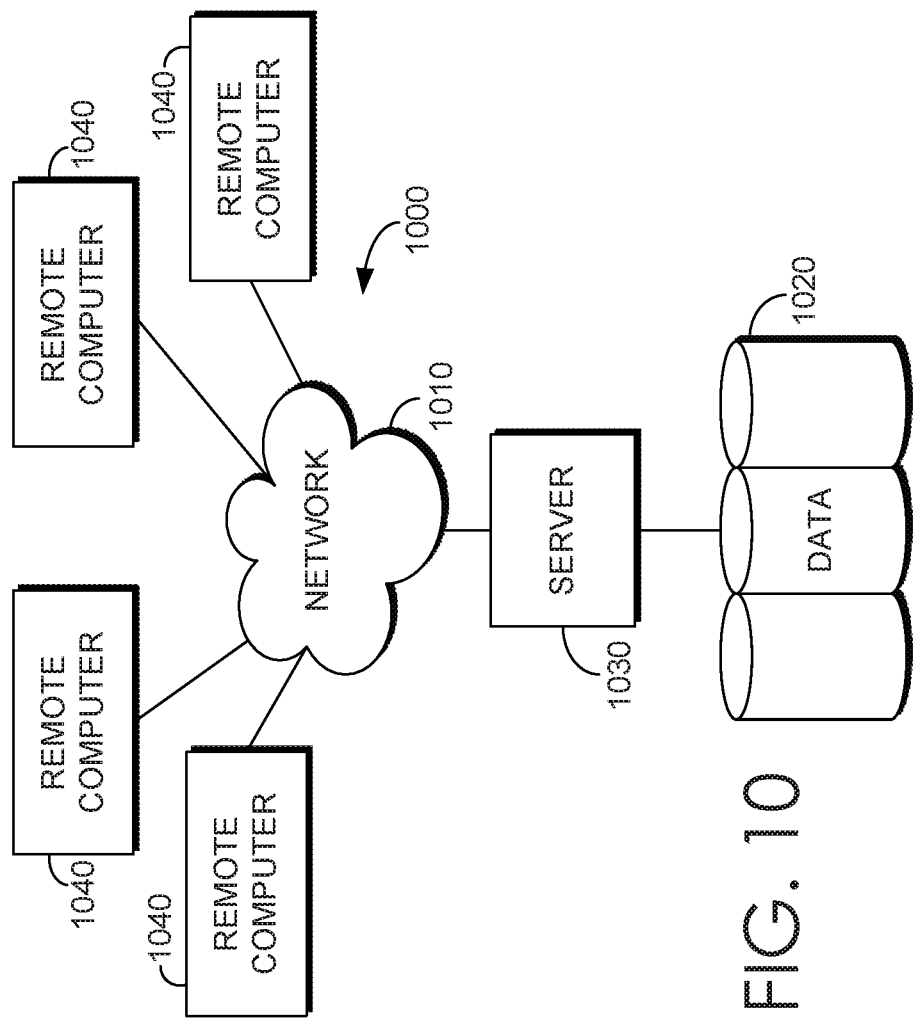
FIG. 10 is a simplified schematic view of an exemplary computing environment useful in practicing some aspects of this disclosure.

The systems, methods, and media described may be operated in an exemplary computing environment 1000 as shown in FIG. 10. Exemplary computing environment 1000 includes at least one computing device in the form of a control sever 1030. Components of control server 1030 may include, without limitation a processing unit, internal system memory, and a suitable system bus for coupling various system components, including database cluster 1020, with the control server 1030. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus.

The control server 1030 typically includes therein, or has access to, a variety of computer-readable media, for instance, database cluster 1020. Computer-readable media can be any available media that may be accessed by control server 1030, and includes volatile and nonvolatile media, as well as removable and non-removable media. By way of example, and not limitation, computer-readable media may include computer-storage media and communication media. Computer-storage media may include, without limitation, volatile and nonvolatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 1030. Computer-storage media may exclude signals per se. Computer-readable media may exclude signals per se.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media. The computer-storage media discussed above and illustrated in FIG. 10, including database cluster 1020, provide storage of computer readable instructions, data structures, program modules, and other data for the control server 1030.

The control server 1030 may operate in a computer network 1010 using logical connections to one or more remote computers 1040. Remote computers 1040 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices and the clinician's home or the patient's own home or over the Internet. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 1040 may also be physically located in non-traditional medical care environments so that the entire health care community may be capable of integration on the network. The remote computers 1040 may be personal computers, servers, routers, network PCs, peer devices, other common network nodes, or the like, and may include some or all of the elements described above in relation to the control server 1030. The devices can be personal digital assistants or other like devices. As described above, one or more of the remote computers 1040 may be specifically designed and/or configured to perform certain functions in relation to the systems and methods disclosed, distinguishing those devices from general purpose computers.

Exemplary computer networks 1010 may include, without limitation, local area networks (LANs) and/or wide area networks (WANs). Such networking environments are commonplace in offices, enterprise-wide computer networks, intranets, and the Internet. When utilized in a WAN networking environment, the control server 1030 may include a modem or other means for establishing communications over the WAN, such as the Internet. In a networked environment, program modules or portions thereof may be stored and/or executed on the control server 1030, in the database cluster 1020, or on any of the remote computers 1040. For example, and not by way of limitation, various application programs and/or data may reside on the memory associated with any one or more of the remote computers 1040. It will be appreciated by those of ordinary skill in the art that the network connections shown are exemplary and other means of establishing a communications link between the computers (e.g., control server 1030 and remote computers 1040) may be utilized.

In operation, a user may enter commands and information into the control server 1030 or convey the commands and information to the control server 1030 via one or more of the remote computers 1040 through input devices, such as a keyboard, a pointing device (commonly referred to as a mouse), a trackball, a touchscreen or a touch pad. Other input devices may include, without limitation, microphones, satellite dishes, scanners, or the like. Commands and information may also be sent directly from a remote healthcare device to the control server 1030. In addition to a monitor, the control server 1030 and/or remote computers 1040 may include other peripheral output devices, such as speakers and a printer.

Many other internal components of the control server 1030 and the remote computers 1040 are not shown because such components and their interconnection are well known. Accordingly, additional details concerning the internal construction of the control server 1030 and the remote computers 1040 are not further disclosed herein.

Methods and systems of embodiments of the present disclosure may be implemented in a WINDOWS or LINUX operating system, operating in conjunction with an Internet-based delivery system. One of ordinary skill in the art will recognize that the described methods and systems can be implemented in any alternate operating system suitable for supporting the disclosed processing and communications. As contemplated, the methods and systems of embodiments of the present disclosure may also be implemented on a stand-alone desktop, personal computer, cellular phone, smart phone, PDA, or any other computing device used in a healthcare environment or any of a number of other locations. Nonetheless, when networked and/or programmed as described herein, the system does more than the individual, generic devices could do.

It will be appreciated by one of skill in the art that the methods disclosed may be performed by one or more computing devices executing instructions embodied on computer-readable media. The instructions may cause the one or more computers to perform the method steps disclosed when executed by one or more processors associated with the one or more computers. Such media may be embodied in hardware, firmware, computer storage media, computer-readable media, or other devices or technologies now known or later arising.

Computer-readable media embodying one or more computer executable instructions may include a data acquisition module. The data acquisition module may acquire data from one or more 3D motion sensors 120. The data acquisition module may receive data sent to it by one or more devices, or may request or retrieve data from one or more devices. The data acquisition module may further acquire data from one or more databases and/or electronic files available to the system, such as an EHR system, a database containing photographs or other identifiers for patients and/or caregivers, or any other system or file containing useful information.

A virtual barrier module may define and/or provide a user interface for defining, altering, and/or confirming a virtual barrier. The virtual barrier module may use the virtual barrier to create one or more subsets of data acquired by the data acquisition module. For example, a subset of data limited from the entire field of view of a 3D motion sensor may be generated for only data from within a virtual barrier or within a specified distance of a virtual barrier. Analysis of the data may be limited to the subset of data, so as to conserve processing capacity in the system by not analyzing data from portions of the field of view that are unlikely to be relevant to whether or not the virtual barrier has been crossed. Similarly, subsets of data may be defined for communication and/or storage purposes, to conserve communications bandwidth and/or storage capacity requirements for the system.

A person identification module may be configured to analyze data acquired by the data acquisition module, and/or subsets of data acquired by the data acquisition module. The person identification module may classify objects in images from one or more 3D motion sensors, and identify objects that meet a minimum confidence threshold for classification as a person. The person identification module may further use facial recognition, ID tokens (including RFID or other signaling tokens), ID markers (including bar codes, name tags, and the like), or other identifiers to identify the patient as an individual. If the data acquisition module has accessed patient files or other sources of identifiers for patients, caregivers or clinicians, the person identification module may compare data from the 3D motion sensors or other sensors (e.g., RFID readers) with other information to identify the person individually, e.g., by name or patient number. Alternately, facial recognition or other biometric data may be used to distinguish one person from other people who may be in or come in and out of the images, such as visitors, caregivers, clinicians, etc., without identifying the person by name. Identifying or distinguishing a person individually may be helpful if more than one person is present in the image, e.g., to prevent sending alarms when a visitor crosses a virtual barrier intended for a patient, or when a patient crosses a virtual barrier intended for a caregiver (e.g., a boundary that the caregiver should not cross without washing his or her hands).

An alert module may monitor the position of any bounding boxes relative to the virtual barrier. The alert module may generate an alert if the bounding box touches or crosses the virtual barrier, or if a specified minimum portion of the bounding box crosses the virtual barrier. If the bounding box, the virtual barrier, or both is an open figure or includes irregular boundaries (e.g., boundaries which are not straight lines or single-radius curves), an alert may be generated if any portion of the bounding box touches or crosses any portion of the virtual barrier, or if a specified minimum portion of the bounding box crosses any portion of the virtual barrier or a specified minimum portion of the virtual barrier. As with the bounding boxes, portions of the virtual barrier could be measured as a minimum number of pixels, a minimum percent of the pixel area within the virtual barrier, or a minimum percent of the volume of a 3D virtual barrier, and the minimum portion of the virtual barrier could be 0% or any percentage greater than 0% and less than or equal to 100%. An alert may be sent only if the entire bounding box crosses the virtual barrier. An initial alert may be sent if a portion of the bounding box touches or crosses any portion of the virtual barrier, and another alert may be sent if the entire bounding box crosses the virtual barrier. Additional alerts could be sent as progressively larger portions of the bounding box crosses the virtual barrier. For example, if the monitoring is to detect a patient attempting to get out of bed without assistance, as for fall prevention, an alert may be sent if the bounding box touches any portion of the virtual barrier. This alert might not trigger an immediate response, for example, if a caregiver is busy or if the person being monitored is active. However, an alert indicating that 10% of the bounding box has crossed the virtual barrier may be of higher priority, because it is more likely that the patient is continuing to move across the virtual barrier. Similarly, an alert indicating that 20% or 30% or more of the bounding box has crossed the virtual barrier may signal that an immediate response is needed to prevent the patient from leaving the bed unassisted.

A communication module may be configured to receive alerts and/or confirmations from the alert module, and to select and transmit an appropriate message to a patient, a caregiver, an alternate caregiver, other human users, a centralized monitoring station, and/or others. The communication module may select a mode of communication, e.g., an automated phone call, an e-mail, a text display in a patient's room, etc., based on user preferences, default settings, and/or the nature of the message to be communicated. The communication module may select a message based on the nature of the communication (e.g., whether the bounding box has partially or completely crossed the virtual barrier, whether the determination based on the bounding box has been confirmed by alternative analyses and/or human confirmation), and may further select a language for delivering the message. Different modes of communication, different message content and/or different languages may be selected for different alert recipients, or the same alert or confirmation may be sent to all recipients, using the same or different modes of communication for different recipients, if there is more than one recipient.

A central monitoring module may aggregate data from the monitoring of multiple patients. Image data and/or video, if available, may be displayed on a primary display, rendered as human-intelligible images. The central monitoring module may move a display of data related to a patient to an alert display, or duplicate a display of data related to a patient on an alert display, upon receiving an alert for that patient. The central monitoring module may move a display of data related to a patient to a primary display, or may remove a display of data related to a patient from an alert display, after receiving a response to an alert. The central monitoring module may be configured to permit a human attendant using the central monitoring module to access the communication module to send a message to one or more recipients regarding an alert, a response to an alert, a lack of response to an alert, and/or confirmation that an alert condition has been corrected. Messages sent via the central monitoring module may be pre-recorded or pre-determined (e.g., selected from a menu of available messages) or may be recorded, typed, or otherwise entered by the human attendant via the central monitoring module and communication module.

A recordation module may store data related to alerts and/or confirmations, including any received response (e.g., a response entered into the system by a human user), observed response, or the apparent lack of a response to any alert. The data may be stored in a database associated with the system, or in any other desired electronic file or storage location. In some embodiments, the recordation module may store data for a particular patient in an EHR, case report form, or other medical recordkeeping file. In some embodiments, the recordation module may store data in a database or file accessible to an EHR system and/or other systems. In some embodiments, the recordation module may store all data acquired for a particular patient, or only data regarding alerts and/or confirmations, or only data for a designated timeframe.

All steps and flowcharts described herein, including in the attached figures, are meant to be illustrative. It should be understood that other steps may be used with the illustrated steps, and, further, that some steps may be useful without the practice of other steps included in the figures. The illustrated sequence of steps is also exemplary, and, unless described otherwise, the steps may be performed in different sequences, combinations, and/or subcombinations.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. A method of identifying the crossing of a virtual barrier, the method being performed by a computerized monitoring system and comprising:
   receiving image data for a room from one or more 3D motion sensors;
   configuring a virtual barrier within the room;
   classifying an object within the room as a person;
   creating a bounding box to circumscribe at least a portion of the person;
   monitoring a position of the bounding box over time and relative to the virtual barrier; and
   wherein upon detecting that at least a portion of the bounding box has touched or crossed the virtual barrier, initiating skeletal tracking, blob tracking, or a combination thereof to confirm the touching or crossing of the virtual barrier.

2. The method of claim 1, wherein the virtual barrier is configured automatically by the computerized monitoring system.

3. The method of claim 1, wherein the virtual barrier is configured by the computerized monitoring system based on input from a human user.

4. The method of claim 1, further comprising sending an alert to a computerized communication system upon detecting the bounding box touches or crosses the virtual barrier.

5. The method of claim 4, wherein, upon receiving the alert, the computerized communication system notifies the person, a caregiver, or clinician that the virtual barrier has been crossed.

6. The method of claim 4, wherein an alert is sent to the computerized communication system only if a specified minimum portion of the bounding box crosses the virtual barrier.

7. The method of claim 1, further comprising sending the image data to a centralized monitoring station.

8. The method of claim 7, further comprising displaying human-intelligible images from the image data at the centralized monitoring station.

9. A system for identifying the crossing of a virtual barrier, the system comprising:
   a computerized monitoring system in communication with one or more 3D motion sensors; and
   a computerized communication system;
   wherein the computerized monitoring system is configured to:
   receive image data from the one or more 3D motion sensors;
   configure a virtual barrier;
   analyze the image data to create a bounding box around a person in the image data;
   upon detecting that at least a portion of the bounding box has touched or crossed the virtual barrier, initiate skeletal tracking, blob tracking, or a combination thereof to confirm the touching or crossing of the virtual barrier; and
   send an alert to the computerized communication system upon confirmation of the touching or crossing of the virtual barrier.

10. The system of claim 9, further comprising a user input device, wherein the computerized monitoring system is configured to configure the virtual barrier based on user input.

11. The system of claim 9, further comprising a centralized monitoring station configured to display human-intelligible images based on the data from the one or more 3D motion sensors.

12. The system of claim 11, wherein the centralized monitoring station is configured to receive an alert from the computerized communication system, and, upon receipt of the alert, move the display of human-intelligible images to an alert display.

13. The system of claim 9, wherein the virtual barrier is configured automatically by the computerized monitoring system.

14. The system of claim 9, wherein the computerized monitoring system is configured to use biometrics to identify the person.

15. Non-transitory computer-readable media having embodied thereon instructions which, when executed by a computer processor, cause the processor to:
   receive image data for a room from one or more 3D motion sensors;
   configure a virtual barrier within the room, by a computerized monitoring system;
   classify an object within the room as a person;
   create a bounding box to circumscribe at least a portion of the person;
   monitor a position of the bounding box over time and relative to the virtual barrier; and
   wherein upon detecting that at least a portion of the bounding box has touched or crossed the virtual barrier, initiate skeletal tracking, blob tracking, or a combination thereof to confirm the crossing of the virtual barrier.

16. The media of claim 15, wherein the instructions further cause the processor to accept user input to configure the virtual barrier.

17. The media of claim 15, wherein the instructions further cause the processor to send an alert to a computerized communication system upon confirmation that the bounding box touches or crosses the virtual barrier.

18. The media of claim 17, wherein the instructions further cause the processor to send another alert to the computerized communication system if all of the bounding box crosses the virtual barrier.

19. The media of claim 15, wherein the instructions further cause the processor to send the image data to a centralized monitoring station.

* * * * *